United States Patent
Soltani et al.

(10) Patent No.: US 10,973,448 B2
(45) Date of Patent: Apr. 13, 2021

(54) SYSTEM, METHODS AND APPARATUSES FOR IN SITU ELECTROCHEMICAL IMAGING

(71) Applicant: THE GOVERNING COUNCIL OF THE UNIVERSITY OF TORONTO, Toronto (CA)

(72) Inventors: Nima Soltani, Toronto (CA); Roman Genov, Toronto (CA)

(73) Assignee: THE GOVERNING COUNCIL OF THE UNIVERSITY OF TORONTO, Toronto (CA)

( * ) Notice: Subject to any disclaimer, the term of this patent is extended or adjusted under 35 U.S.C. 154(b) by 604 days.

(21) Appl. No.: 15/580,823

(22) PCT Filed: Jun. 9, 2016

(86) PCT No.: PCT/CA2016/050655
§ 371 (c)(1),
(2) Date: Dec. 8, 2017

(87) PCT Pub. No.: WO2016/197245
PCT Pub. Date: Dec. 15, 2016

(65) Prior Publication Data
US 2018/0214054 A1    Aug. 2, 2018

Related U.S. Application Data

(60) Provisional application No. 62/173,066, filed on Jun. 9, 2015.

(51) Int. Cl.
*A61B 5/05*    (2021.01)
*A61B 5/1473*  (2006.01)
(Continued)

(52) U.S. Cl.
CPC ............ *A61B 5/1473* (2013.01); *A61B 5/002* (2013.01); *A61B 5/0536* (2013.01);
(Continued)

(58) Field of Classification Search
CPC ..... A61B 5/1473; A61B 5/002; A61B 5/0536; A61B 5/1477; A61B 5/6868;
(Continued)

(56) References Cited

U.S. PATENT DOCUMENTS 6,597,954 B1    7/2003  Pless et al.
7,212,110 B1    5/2007  Martin et al.
(Continued)

FOREIGN PATENT DOCUMENTS

| CN | 102157989 | 8/2011 |
| WO | 2008/109508 A2 | 9/2008 |
| WO | 2015092747 A2 | 6/2015 |

OTHER PUBLICATIONS

Abdelhalim, Karim, et al., "64-Channel UWB Wireless Neural Vector Analyzer SOC With a Neurostimulator", IEEE Journal of Solid-state circuits, IEEE, USA, vol. 48, No. 10, Oct. 1, 2013, p. 2494-2510.
(Continued)

*Primary Examiner* — Christian Jang
(74) *Attorney, Agent, or Firm* — Bhole IP Law; Anil Bhole; Marc Lampert

(57) ABSTRACT

Systems, methods and apparatuses described herein generally provide a millimetre size package-free complementary metal-oxide-semiconductor ("CMOS") chip (referred to as a "die") for the in situ (on-site) measurement or imaging of electrochemically detectable analytes.

6 Claims, 35 Drawing Sheets

(51) Int. Cl.
- A61B 5/00 (2006.01)
- A61B 5/0536 (2021.01)
- A61B 5/1477 (2006.01)
- H03M 3/00 (2006.01)
- A61B 5/145 (2006.01)

(52) U.S. Cl.
CPC .......... *A61B 5/1477* (2013.01); *A61B 5/6868* (2013.01); *A61B 5/7225* (2013.01); *H03M 3/464* (2013.01); *A61B 5/0022* (2013.01); *A61B 5/14532* (2013.01); *A61B 5/14546* (2013.01); *A61B 5/4094* (2013.01); *A61B 2560/0219* (2013.01); *H03M 3/43* (2013.01); *H03M 3/462* (2013.01)

(58) Field of Classification Search
CPC . A61B 5/7225; A61B 5/0022; A61B 5/14532; A61B 5/14546; A61B 2560/0219; A61B 5/4094; H03M 3/464; H03M 3/43; H03M 3/462

See application file for complete search history.

(56) References Cited

U.S. PATENT DOCUMENTS

| | | | |
|---|---|---|---|
| 8,180,452 B2 | 5/2012 | Shaquer | |
| 9,030,239 B1* | 5/2015 | Dastgheib | G01N 27/48 327/132 |
| 2002/0172069 A1* | 11/2002 | Thompson | G11C 11/22 365/145 |
| 2004/0068199 A1 | 4/2004 | Echauz et al. | |
| 2007/0067003 A1 | 3/2007 | Sanchez et al. | |
| 2007/0150024 A1 | 6/2007 | Leyde et al. | |
| 2007/0213786 A1 | 9/2007 | Sackellares et al. | |
| 2008/0176271 A1 | 7/2008 | Silver et al. | |
| 2010/0197524 A1 | 8/2010 | Janata et al. | |
| 2011/0130797 A1 | 6/2011 | Talathi et al. | |
| 2011/0306847 A1* | 12/2011 | Lowry | A61B 5/14542 600/301 |
| 2012/0078071 A1 | 3/2012 | Bohm et al. | |
| 2012/0283800 A1 | 5/2012 | Perryman et al. | |
| 2013/0172774 A1 | 7/2013 | Crowder et al. | |
| 2014/0012122 A1 | 1/2014 | Sadek et al. | |
| 2019/0314564 A1 | 10/2019 | Rudser | |

OTHER PUBLICATIONS

Supplementary European Search Report for EU patent application No. 17830150.3, EPO, dated May 8, 2020.
European Search Opinion for EU patent application No. 178301503, EPO, dated May 8, 2020.
Office Action for U.S. Appl. No. 15/766,402; USPTO; dated Jul. 31, 2020.
International Search Report corresponding to PCT/CA2016/050655; Canadian Intellectual Property Office; dated Sep. 7, 2016.
Witten Opinion of the International Searching Authority corresponding to PCT/CA2016/050655; Canadian Intellectual Property Office; dated Sep. 7, 2016.
"The 128-Channel Fully Differential Digital Integrated Neural Recording and Stimulation Interface" Shahrokhi et al [Online], May 24, 2010 (May 24, 2010), [Retrieved on Oct. 12, 2017 (Oct. 12, 2017). Retrieved from: http://ieeexplore.ieee.org/document/5471738/authors?part=1.
"Design of an Optimal & Closed-Loop Neurostimulation System for treatment of Epilepsy" Gao, Richard, [online], Nov. 23, 2015 (Nov. 23, 2015], Retrieved on Oct. 12, 2017 (Oct. 12, 2017). Retrieved from: http:www,undergraduatelibrary.org/2014/medical-sciences/design-optimal-closed-loop-neuromodulation-system-treatment-epilepsy.

"Micropower CMOS Integrated Low-Noise Amplification, Filtering, and Digitization of Multimodal Neuroptentials" Mollazadeh et al. [online], Jan. 1, 2010 (Jan. 1, 2010). Retrieved Oct. 12, 2017 (Oct. 12, 2017). Retrieved from: https://www.ncbi.nlm.nih.gov/pmc/articles/PMC2747318/.
Bagheri, A., et al. (2013) Massively-Parallel Neuromonitoring and Neurostimulation Rodent Headset With Nanotextured Flexible Microelectrodes. IEEE Transactions on Biomedical Circuits and Systems, 7:601-609.
Medeiros, D.D., Moraes M.F. (2014) Focus on Desynchronization Rather Than Excitability: A New Strategy for Intraencephalic Electrical Stimulation. Epilepsy Behav, 38C:32-36.
Jiruska, P., et al. (2010) Effects of Direct Brain Stimulation Depend on Seizure Dynamics. Epilepsia 51:93-97.
Lockman, J., Fisher, R.S. (2009) Therapeutic Brain Stimulation for Epilepsy. Neurologic Clinics 27:1031-1040.
Sun, F.T., Morrell, M.J. (2014) The RNS System: Responsive Cortical Stimulation for the Treatment of Refractory Partial Epilepsy. Expert Review of Medical Devices, 11:563-572.
Krook-Magnuson, E., et al. (2013) On-Demand Optogenetic Control Of Spontaneous Seizures in Temporal Lobe Epilepsy. Nature Communications, 4:1376.
Weiss, S.R., et al., (1995) Quenching: Inhibition of Development and Expression of Amygdala Kindled Seizures With Low Frequency Stimulation. Neuroreport, 6:2171-2176.
Tergau, F., et al. (1999) Low-Frequency Repetitive Transcranial Magnetic Stimulation Improves Intractable Epilepsy. Lancet, 353:2209.
Koubeissi, M.Z. et al., (2013) Low-Frequency Electrical Stimulation of a Tiber Tract in Temporal Lobe Epilepsy. Annals of Neurology, 74:223-231.
Colpan, M.E., et al., (2007) Proportional Feedback Stimulation for Seizure Control in Rats. Epilepsia, 48:1594-1603.
Good, L.B. et al., (2009) Control of Synchronization of Brain Dynamics Leads to Control of Epileptic Seizures in Rodents. International Journal of Neural Systems, 19:173-196.
Rashid, S. et al. (2012)Low Frequency Stimulation of Ventral Hippocampal Commissures Reduces Seizures in a Rat Model of Chronic Temporal Lobe Epilepsy. Epilepsia, 53:147-156.
Osorio, I., Frei M.G. (2009) Seizure Abatement With Single DC Pulses: Is Phase Resetting at Play? International Journal of Neural Systems, 19:149-156.
International Search Report corresponding to PCT/CA2016/051169; Canadian Intellectual Property Office; dated Jan. 13, 2017.
Written Opinion of the International Searching Authority corresponding to PCT/CA2016/051169; Canadian Intellectual Property Office; dated Jan. 13, 2017.
International Search Report corresponding to PCT/2017/050867; Canadian Intellectual Property Office; dated Oct. 18, 2017.
Written Opinion of the International Searching Authority corresponding to PCT/CA2017/050867; Canadian Intellectual Property Office; dated Oct. 18, 2018.
Office Action for U.S. Appl. No. 15/177,615; USPTO; dated Oct. 6, 2017.
Office Action for U.S. Appl. No. 15/177,615; USPTO; dated Nov. 1, 2018.
Office Action for U.S. Appl. No. 15/177,615; USPTO; dated Aug. 9, 2018.
Schindler et al., "Increasing synchronization may promote seizure termination: Evidence from status epilepticus", Jun. 18, 2007, Clinical Neurophysiology, 118, 1955-1968.
Office Action for U.S. Appl. No. 15/177,615; USPTO; dated Dec. 31, 2018.
Advisory Action for U.S. Appl. No. 15/177,615; USPTO; dated Oct. 2, 2018.
Advisory Action for U.S. Appl. No. 15/177,615; USPTO; dated Jan. 30, 2019.
Supplementary Partial European Search Report for EU patent application No. 16806476.4, EPO, dated Feb. 14, 2019.
Panagiotis Kassanos et al: ACMOS Magnitude/Phase Measurement Chip for Impedance Spectroscopy, IEEE Sensors Journal, vol. 13, No. 6, Jun. 2013.
Supplementary Partial European Search Report for EU patent application No. 16852943.6, EPO, dated Apr. 11, 2019.

(56) References Cited

OTHER PUBLICATIONS

Kassiri, Hossein et al.: Inductively-powered direct-coupled 64-channel chopper-stabilized epilepsy-responsive neurostimulator with digital offset cancellation and tri-band radio, 2013 Proceedings of the ESSCIRC (ESSCIRC), IEEE, Sep. 22, 2014, pp. 95-98.
Soltani, Nima et al., Cellular inductive powering system for weakly-linked resonant rodent implants, 2013 IEEE Biomedical Circuits and Systems Conference (Biocas), IEEE, Oct. 31, 2013, pp. 350-353.
European Search Opinion for EU patent application No. 16852943.6, EPO, dated Apr. 11, 2019.
Supplementary European Search Report for EU patent application No. 16806476.4, EPO, dated Jun. 18, 2019.
European Search Opinion for EU patent application No. 16806476.4, EPO, dated Jun. 18, 2019.
Panagiotis Kassanos et al: A CMOS magnitude/phase measurement chip for impedance spectroscopy, IEEE Sensors Journal, IEEE Service Center, New York, NY, US, vol. 13, No. 6, Jun. 1, 2013 (Jun. 1, 2013), pp. 2229-2236, XP011506442, ISSN: 1530-437X, DOI: 10.1109/JSEN.2013.2251628.

\* cited by examiner

SYSTEM, METHODS AND APPARATUSES FOR IN SITU ELECTROCHEMICAL IMAGING

TECHNICAL FIELD

Systems, methods and apparatuses for in situ measurement and imaging of electrochemically detectable analytes.

BACKGROUND

Micro-scale chips can be implanted or otherwise positioned in situ on a subject to measure target analytes. Integrating measurement functions of laboratory techniques into micro-scale implantable chips has myriad possible advantages, including added convenience and accuracy of measurement. Excessive power draw from components of implantable micro-scale chips can limit utility.

SUMMARY

In one aspect, an integrated circuit for electrochemically measuring target analytes in a subject is provided, the integrated circuit comprising: a recording module array coupled to a plurality of microelectrodes disposable on, in or adjacent to the subject for recording analog signals relating to chemically bonded analytes of the subject; an op-amp-less delta-sigma-ADC-based potentiostat circuit for providing a digitized representation of the recorded analog signals, the potentiostat circuit comprising: an op-amp less integrator circuit coupled to the recording module array, the integrator circuit comprising a grounded capacitor for integration of the recorded analog signal; a comparator coupled to an output of the integrator circuit to reduce signal distortion thereof; a digital-to-analog converter providing a negative feedback loop from an output of the comparator to the output of the integrator circuit; and a pulse shaping block providing an output signal of the potentiostat; and an impedance spectroscopy circuit coupled to the output signal of potentiostat comprising a 1 bit XOR gate and a counter for receiving a waveform and the output signal, and providing a 1 bit multiplication of the output signal.

In another aspect, a potentiostat circuit is provided, the potentiostat circuit comprising: an op-amp-less integrator circuit comprising a grounded capacitor for integration of the recorded analog signal; a comparator coupled to an output of the integrator circuit to reduce signal distortion thereof; a digital-to-analog converter providing a negative feedback loop from an output of the comparator to the output of the integrator circuit; and a pulse shaping block providing an output signal of the potentiostat.

In a further aspect, an integrated circuit for electrochemically measuring target analytes of a subject is provided, the integrated circuit comprising: a power coil for receiving power from a receiver device by magnetic induction; a microelectrode array and an associated amperometric channel array for measuring the target analytes of the subject and generating sensor readings; and a transmitter for wirelessly transmitting sensor readings to the receiver device.

In yet another aspect, a method for in situ electrochemical imaging of target analytes of a subject is provided, the method comprising: implanting an integrated circuit on, in or adjacent to a targeted region of the subject, the integrated circuit comprising: a power coil for receiving power from a receiver device by magnetic induction; a microelectrode array and an associated amperometric channel array for measuring the target analytes of the subject and generating sensor readings; and a transmitter for transmitting sensor readings to the receiver device; positioning the receiver device on a surface of the subject; receiving sensor readings at the receiver device; and processing the sensor readings to diagnose risk of seizure onset in the subject.

These and other aspects are contemplated and described herein. It will be appreciated that the foregoing summary sets out representative aspects of systems, methods, apparatuses for in situ electrochemical imaging to assist skilled readers in understanding the following detailed description.

DESCRIPTION OF THE DRAWINGS

A greater understanding of the embodiments will be had with reference to the Figures, in which.

DETAILED DESCRIPTION

Figure 1:
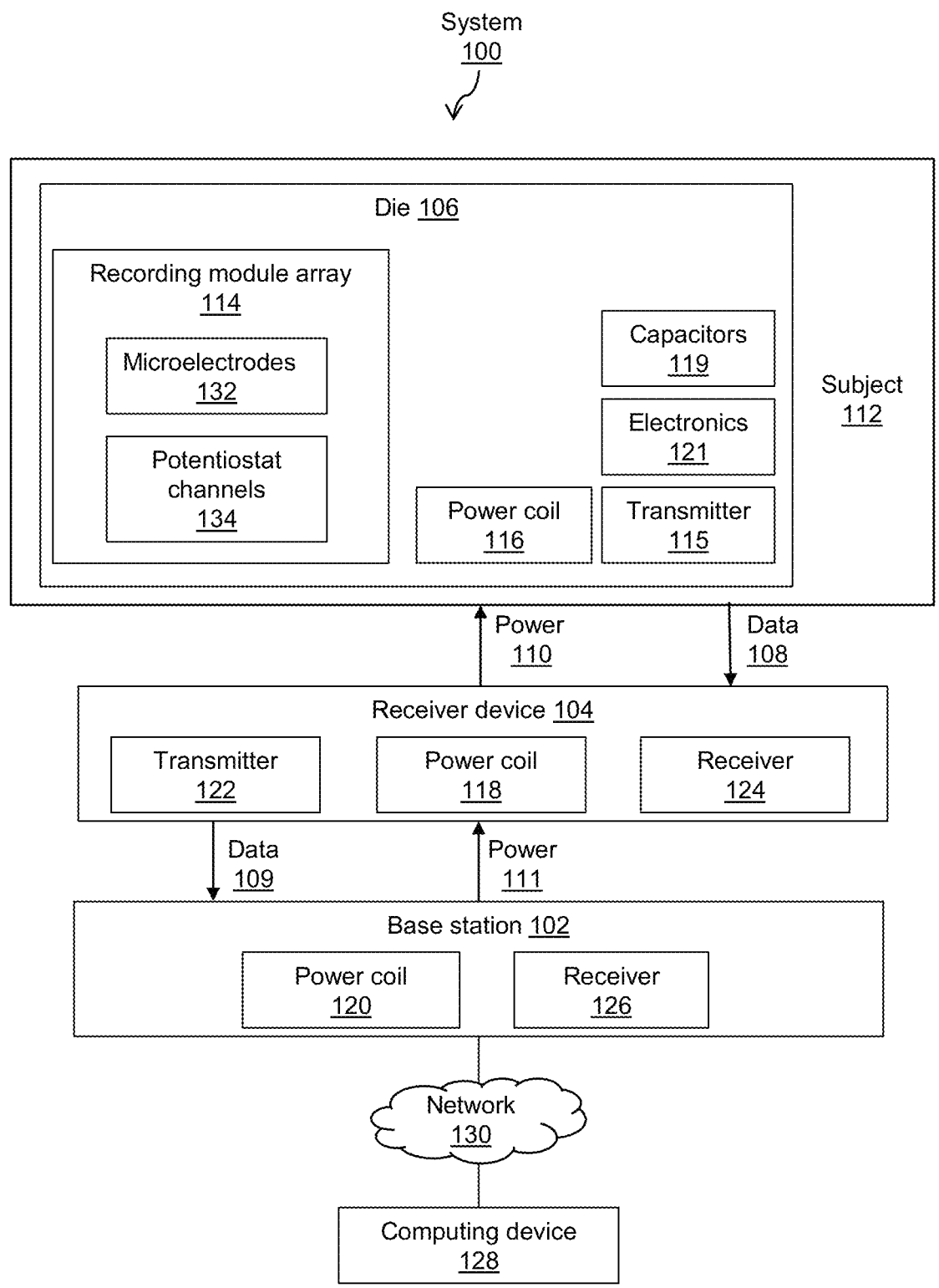
FIG. 1 shows a block diagram of an embodiment of a system for in situ electrochemical imaging.

For simplicity and clarity of illustration, where considered appropriate, reference numerals may be repeated among the Figures to indicate corresponding or analogous elements. In addition, numerous specific details are set forth in order to provide a thorough understanding of the embodiments described herein. However, it will be understood by those of ordinary skill in the art that the embodiments described herein may be practised without these specific details. In other instances, well-known methods, procedures and components have not been described in detail so as not to obscure the embodiments described herein. Also, the description is not to be considered as limiting the scope of the embodiments described herein.

Various terms used throughout the present description may be read and understood as follows, unless the context indicates otherwise: "or" as used throughout is inclusive, as though written "and/or"; singular articles and pronouns as used throughout include their plural forms, and vice versa; similarly, gendered pronouns include their counterpart pronouns so that pronouns should not be understood as limiting anything described herein to use, implementation, performance, etc. by a single gender. Further definitions for terms may be set out herein; these may apply to prior and subsequent instances of those terms, as will be understood from a reading of the present description.

Any module, unit, component, server, computer, terminal or device exemplified herein that executes instructions may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by an application, module, or both. Any such computer storage media may be part of the device or accessible or connectable thereto. Further, unless the context clearly indicates otherwise, any processor or controller set out herein may be implemented as a singular processor or as a plurality of processors. The plurality of processors may be arrayed or distributed, and any processing function referred to herein may be carried out by one or by a plurality of processors, even though a single processor may be exemplified. Any method, application or module herein described may be implemented using computer readable/executable instructions that may be stored or otherwise held by such computer readable media and executed by the one or more processors.

Embodiments described herein generally provide an integrated circuit for electrochemically measuring target analytes. More specifically, an embodiment is a millimetre size package-free complementary metal-oxide-semiconductor ("CMOS") chip (referred to below as "die") for the in situ (on-site) high-spatial resolution measurement or imaging of electrochemically detectable analytes, as well as associated systems, methods and apparatuses. These analytes may, for example, include cellular ions such as Na+, K+, Ca++ Mg; neurotransmitters such as dopamine and serotonin; glucose, insulin and other like molecules; electrolytes; drug concentrations; and other analytes such as glutamate, lactate, noradrenaline, acetylcholine, choline, etc. The term "in situ" includes disposing the integrated circuit or an electrode coupled to the integrated circuit on, in or adjacent to a target region of the subject such that analyte measurements can be obtained from the target region.

Embodiments of a die comprising an induction power coil, as well as an electrode array and an associated amperometric recording channel array for measuring target analytes are described. An inductive power transfer system and a short-range communication circuit power and communicate with the die simultaneously. Further, embodiments of an amperometric channel are described which may minimize size and power consumption by merging circuit blocks and simplifying the resulting schematic as compared to conventional designs based on known properties of the expected channel input signal. Circuit minimization steps are described, including providing a front-end digital op-amp—less potentiostat, and, with respect to the described channel's counter, approximating multiplication coefficients by a single bit approximation of those values.

Thus, embodiments described herein provide an ultra-low power op-amp-less delta-sigma-ADC-based potentiostat circuit. The delta-sigma-ADC-based potentiostat may consume approximately 50 Nanowatts of power. Compared with current op-amp-based potentiostats with the same noise performance, this op-amp-less circuit may provide a significant reduction of power consumption without comprising speed or noise performance as in some other ultra-low power designs. By removing the front-end op-amp, this design may maintain high-speed and low 1/f noise despite being ultra-low power. Moreover, as compared with some other non-amplifier-based ultra-low power potentiostats, this potentiostat may have faster response and lower power consumption. Some embodiments of the potentiostat may, in some circumstances, have more than 1000 times faster response and 50 times less power consumption than some other non-amplifier-based ultra-low power potentiostats.

Further, embodiments described herein provide a computationally-efficient impedance spectroscopy ("IS") circuit which may minimize required computational power. Unlike conventional IS circuits which multiply the potentiostat output by high-resolution $\sin(\omega_o t)$ and $\cos(\omega_o t)$ waveforms, the described IS circuit only multiplies by a 1-bit waveform ("1" when $\sin(\omega_o t)/\cos(\omega_o t)>1$ and "0" when $\sin(\omega_o t)/\cos(\omega_o t)<0$). A single XOR gate replaces the many digital logic gates of conventional IS circuits.

Further, embodiments described herein provide a zero-hysteresis comparator circuit which may reduce or eliminate the signal distortion occurring due to removing the op-amp in embodiments of the potentiostat described herein. This circuit may reduce naturally occurring hysteresis in the comparator by isolating the output of the comparator from its input, which may minimize the impact of the previous comparator output on its current decision.

Referring now to FIG. 1, shown therein is a block diagram of an embodiment of a system 100 for in situ electrochemical imaging. The system 100 comprises a base station 102, an optional receiver device 104 and a die 106, the components and functionality of which will be described in more detail below. In use, the die may be positioned in situ for measurement of target analytes of a subject 112.

The die 106 comprises a recording module array 114 comprising chemically-sensitive microelectrodes 132 and associated potentiostat channels 134 for recording signals relating to chemically bonded analytes, a transmitter 115 for transmitting data relating to the sensor readings, a power coil 116 for receiving energy by magnetic induction from the receiver device 104 or base station 102, low-power electronics 121, and a bank of capacitors 119 for storing energy on the die to power the low-power electronics 121. More particularly, die 106 may be covered along a surface thereof with amperometric recording microelectrodes for bonding chemically with targeted analytes when the die is positioned at a location of interest of a subject 112, in situ, and activated.

The receiver device 104 comprises a transmitter 122, a receiver 124 and a power coil 118. The base station 102 comprises a receiver 126 and a power coil 120. The die 106, receiver device 104 and base station 102 comprise other components as set out in more detail below with reference to particular embodiments.

In the embodiment illustrated in FIG. 1, the die 106 transmits data comprising recorded signals (illustrated as block 108) to the receiver device 104, and receives power therefrom (illustrated as block 110). Similarly, the receiver device 104 transmits data received from the die to the base station 102 and receives power therefrom, as illustrated by blocks 109 and 111, respectively. The base station 102 may be communicatively linked over a wired or wireless network 130 with a computing device 128 for processing received data. Optionally, data may be processed locally at the base station 102 if the base station comprises hardware for processing the data. In embodiments described below, the die 106 may be directly linked with the base station 102.

Figure 2:
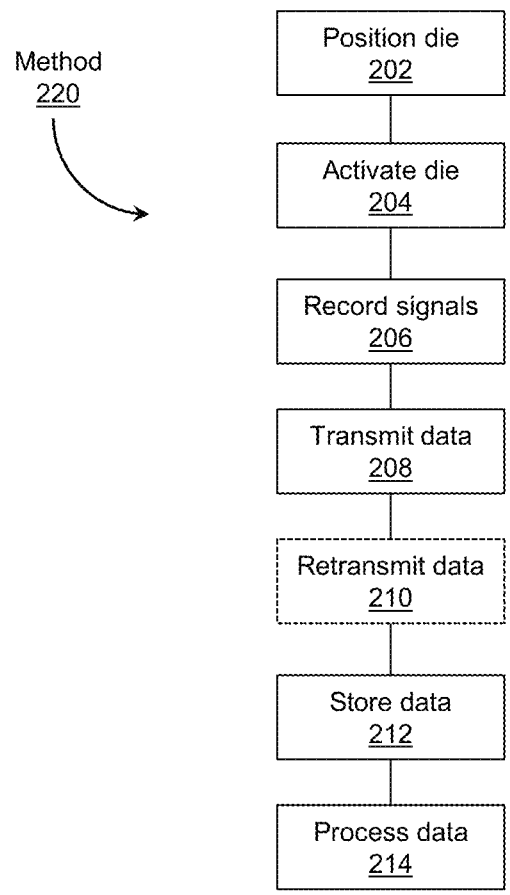
FIG. 2 shows an embodiment of a method for in situ electrochemical imaging.

Referring now to FIG. 2, shown therein is a method 220 for in situ electrochemical imaging. According to the method 220 at block 202 the die 106 is positioned at a location of interest in or on a subject 112. This location might be, for example, adjacent to the subject's eye, brain, or other tissue for which analyte monitoring is desired. At block 204 the die is activated by the placement of a receiver device 104 or base station 102 nearby and the transmission of power to the die. At block 206 the die records signals indicative of the concentration of target analytes, such as ions, molecules, or microorganisms within the particular location that make contact with the die microelectrodes. At block 208, the die sends out the recorded data using radio-frequency ("RF") waves via the transmitter 115 to the receiver device 104 (or directly to the base station 102), positioned nearby, and preferably situated as close as possible to the die 106. At block 210, the data comprising the recorded signals may be buffered and re-transmitted to another RF receiver unit (referred to generally as base station 102) which could be farther away (e.g. meters or further) from the die 106 and the first receiver device 104. At block 212, the data may be stored in memory at the receiver device 104 (or base station 102, if re-transmitted at block 210). At block 214, the data may be processed, either at the receiver device 104, base station 102 or at a communicatively linked computing device, depending on the configuration of the system.

In the following discussion, reference will be made to various figures, each of which is to be referenced along with FIG. 1.

Figure 3:
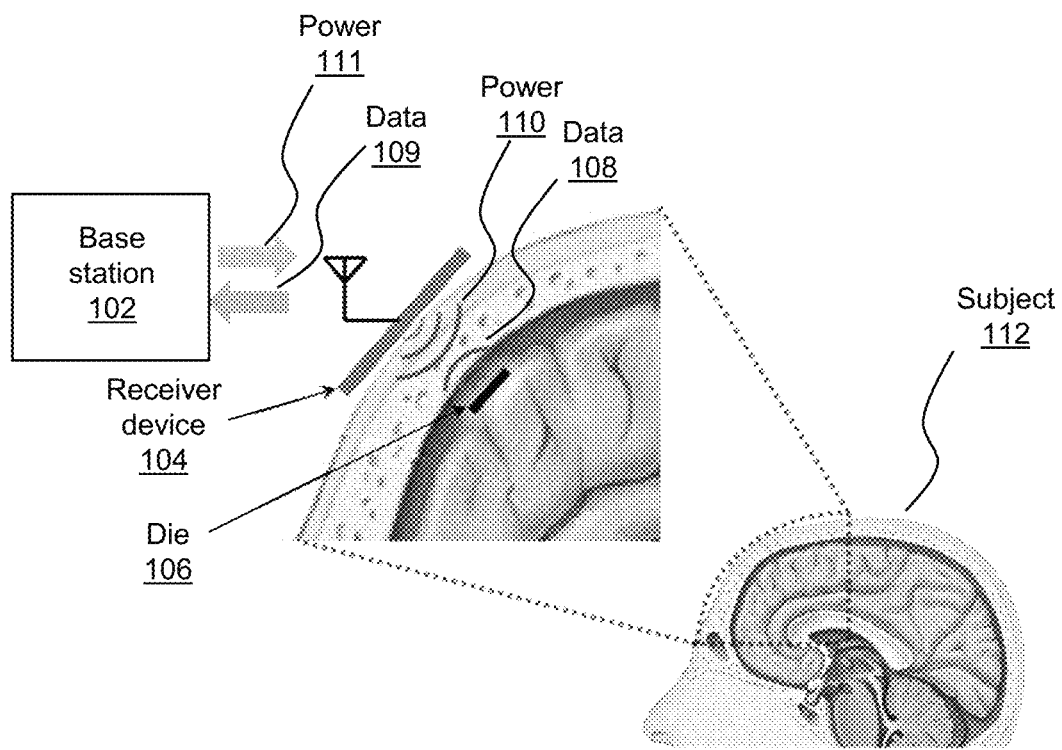
FIG. 3 shows application of a system for in situ electrochemical imaging for selective imaging of the concentrations of potassium (K+) ions over sodium (Na+) ions.

Referring now to FIG. 3, shown therein is a particular application of the system 100 for implementing method 220, applying the in situ CMOS die 106 for selective imaging of concentrations of potassium (K+) ions over sodium (Na+) ions across the implanted region on the cortex of a free-moving patient 112. The die surface takes a 2-dimensional image of analyte concentration profile by simultaneously conducting impedance spectroscopy at all individual microelectrode sites in parallel and converting the resulting signals to digital words at the electrode location in the die, which corresponds to actions carried out at block 206 of method 220. The digital bit stream created from all the microelectrodes data—i.e. impedance spectroscopy information from all individual on-chip microelectrodes in the die—is transmitted wirelessly outside the body to a receiver device 104, which corresponds to block 208. Specifically, a miniature radio comprising a transmitter on the die communicates the recorded information to the receiver device 104. As illustrated, the receiver device 104 may be worn and may be placed on the surface of the subject's skin 112 as close as practically possible to the implanted die. The receiver device 104 may thus be constructed as a flexible patch. The wearable receiver device 104 then re-transmits this information by a more powerful radio to a base station 102 such as a handheld unit or a PC for analysis and display and/or permanent storage, which corresponds to blocks 210, 212, 214. The ionic concentrations provided from the imaging information may be useful for the diagnosis and possible abortion of seizure onsets in patients with intractable epilepsy.

It will be understood that the application provided in FIG. 3 is merely illustrative. It is contemplated that the die 106 could also be used for in situ measurement in other locations of interest. For example, the die could be fabricated into a contact lens for measurement of glucose levels or other analytes along the surface of the eye. Description below of particular embodiments with respect to the application provided in FIG. 3 is not intended to be limiting.

Figure 4:
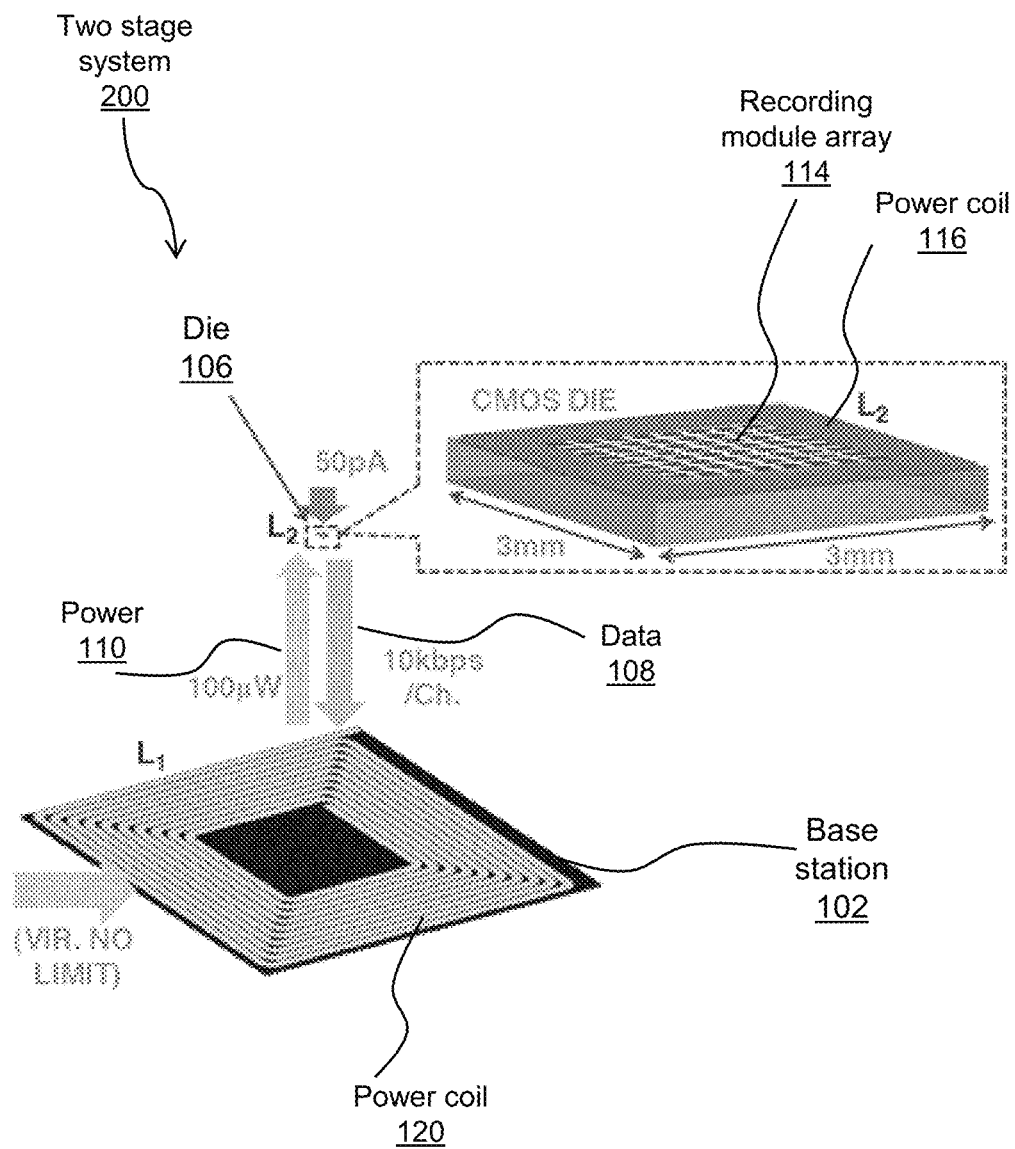
FIG. 4 shows an embodiment of a two-stage system for in situ electrochemical imaging.
Figure 5:
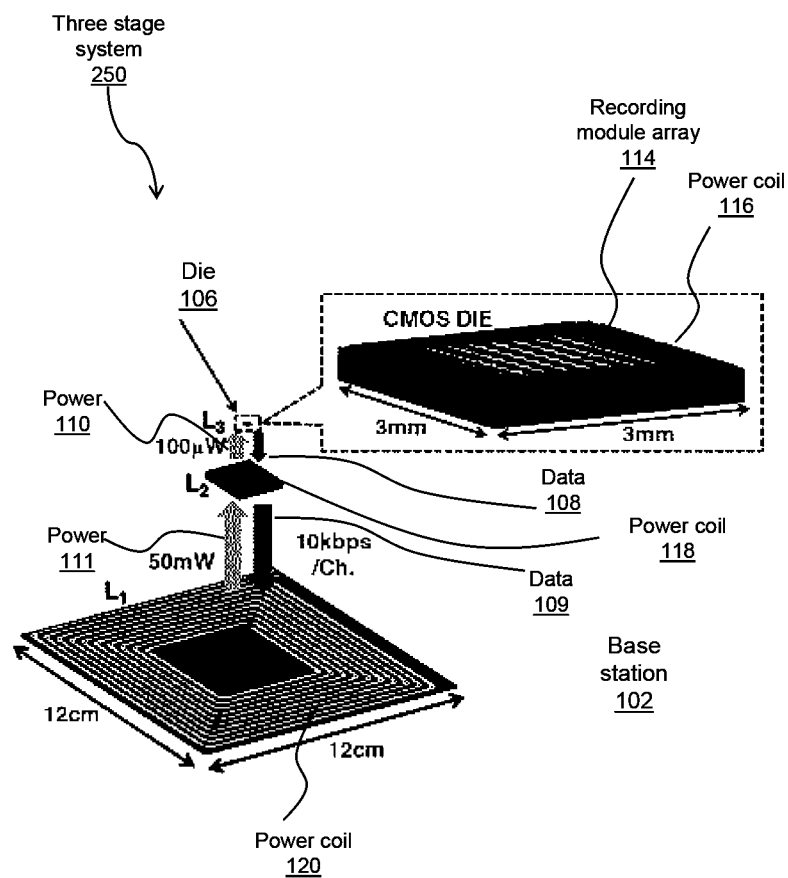
FIG. 5 shows an embodiment of a three-stage system for in situ electrochemical imaging.

Referring now to FIGS. 4 and 5, shown therein are further embodiments of systems for in situ electrochemical imaging 200, 250. The dimensions, power/current usage and bandwidth shown are exemplary and not intended as limiting. The embodiments shown illustrate a two stage system 200 and a three stage system 250 used to wirelessly link the die 106 to the base station 102. Depending on the application, the die 106 can communicate directly with the base station 102 in a two stage system illustrated in FIG. 4, comprising stages L1 and L2. Alternately, according to a three stage system comprising stages L1, L2 and L3, a receiver device 104 may be provided at a second intermediary stage L2, to link with the base station 102, as shown in FIG. 5.

The two stage system 200 may be used when the base station 102 can be located close to the die 106 (such as within a few centimeters). In applications where the base station 102 cannot be located close to the die at all times, the three stage system 250 can be used whereby a receiver device 104 is provided at an intermediate stage, as illustrated in FIG. 5 to relay the data from the die to the base station located some distance from the die (such as a few meters). An advantage of providing the receiver device 104 at an intermediate stage in a three stage system 250 is that it may improve the die performance and the wireless link quality in applications where the base station cannot be present near the die at all times. The intermediate stage is mobile, does not have an energy source attached to it, and is a fraction of the size of the base station. Therefore, in an application such as in FIG. 3, it can be permanently attached at the nearest point to the die to improve die performance and wireless link quality.

As described above with reference to FIG. 1, the energy to power the CMOS die 106 is delivered via magnetic induction from the receiver device 104 or base station 102 (illustrated as element 110 and 111, respectively). In the two stage system 200, the base station 102 generates an alternating magnetic field in coil 120 which is induced into an integrated power coil 116 in the die. The magnetic energy is then converted to electric energy which is stored on a bank of capacitors 119 on the die to power components of the die, including low-power electronics 121. In the three-stage system, the magnetic field created by the base station 102 is induced into a coil 118 in the intermediate stage device 104 which then refocuses the magnetic field to better power the CMOS die. Operable geometries for the magnetic coil in each stage, L1, L2, and L3, would be apparent to those of skill in the art and exemplary geometries are shown in FIG. 5 as 12 cm×12 cm for the base station 102 power coil 120 and 3 mm×3 mm for the die 106 power coil 116, and further geometries are described below.

Data transfer between the CMOS die 106 and the base station 102 or receiver device 104 at element 108 may take place using either of two low-power radio transmission techniques: (a) ultra-wideband pulse radio ("UWB-IR") transmission, and (b) backscatter modulation techniques such as done in passive radio-frequency identification ("RFID") tags. As indicated by element 108 in FIG. 4, the CMOS die 106 communicates the data directly to the base station 102 in the two stage system 200. A UWB-IR transmitter may be used in the two stage system to accomplish this. In the three stage system 250, the data may be backscattered to the intermediate stage at element 108 (as shown in FIG. 4). The data may then be relayed to the base station using a UWB-IR transmitter on the intermediate device 104 at element 109.

Referring now to FIGS. 6 to 9, embodiments and components of the receiver device 104 and base station 102 will be described before describing particular embodiments of the die 106 in subsequent figures.

Figure 6:
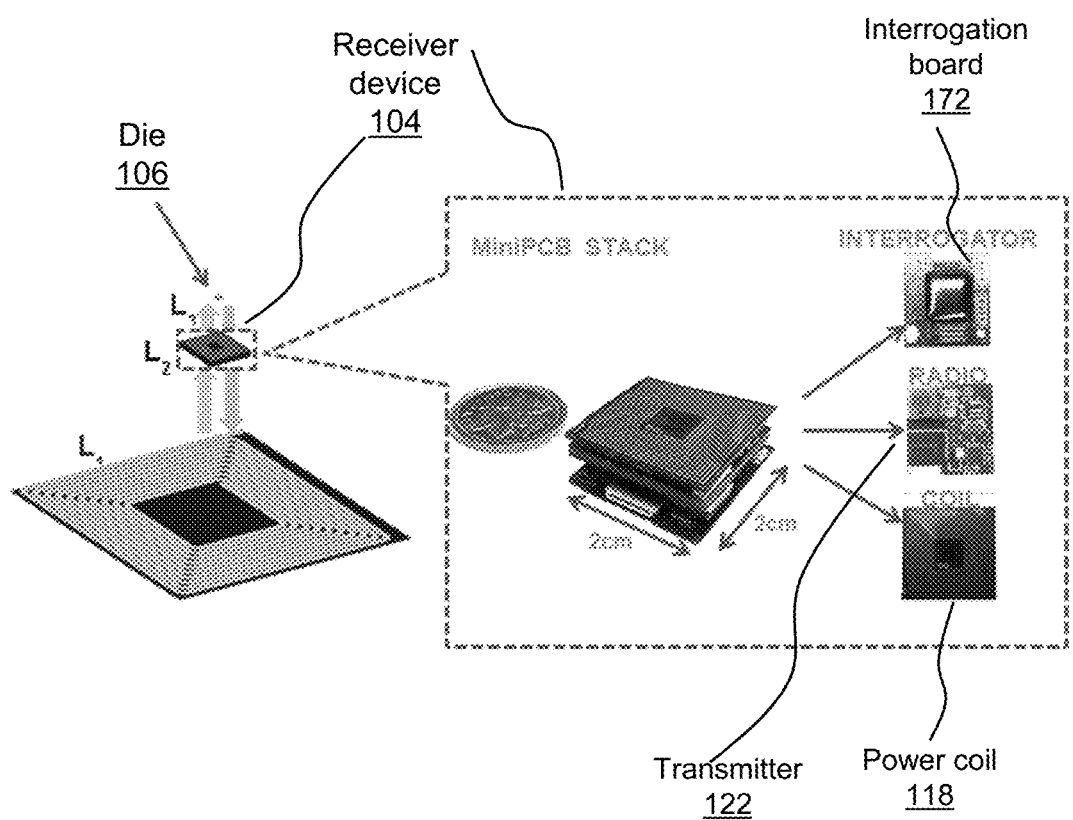
FIG. 6 shows an embodiment of the intermediate receiver device for a system for in situ electrochemical imaging.

Referring now to FIG. 6, shown therein is an embodiment of the intermediate receiver device 104. FIG. 6 shows particularly an embodiment of the receiver device 104 comprising a wireless interrogation microsystem developed on flexible printed circuit boards. As an example, the receiver device 104 may measure approximately 2 cm×2 cm×0.6 cm, as illustrated. During use the receiver device 104 may be worn directly on top of the implant die 106 at the closest point to the die on the exterior of the subject 112 as described above, such as on the surface of the skin. The receiver device 104 comprises an interrogation board 172 comprising a receiver 124 for receiving back telemetry data from the implanted K+ imaging die 106, a small low power short-range radio (optionally 10 mW) comprising a transmitter 122 which may be capable of transmitting up to 1 MBps to a nearby (such as up to 10 m) computer via wireless receiver (e.g., a USB port wireless transceiver dongle 126), and inductive power receiver coil 118 which may comprise a 16-layer spiral inductor developed on a flexible printed circuit board. The transmitted data may be received by the wireless receiver and can be plotted (e.g., in a MATLAB™ interface) for analysis. The coil 118 may include (be joined with) a wideband data coil operating at the third harmonic of the inductive power carrier. The coil 118 receives back telemetry data sent by the implant 106 while blocking the strong power carrier sent by the flexible inductive power receiver board on top of the miniPCB stack. The backtelemetry signal is processed and converted to digital data by the interrogation board.

Figure 7:
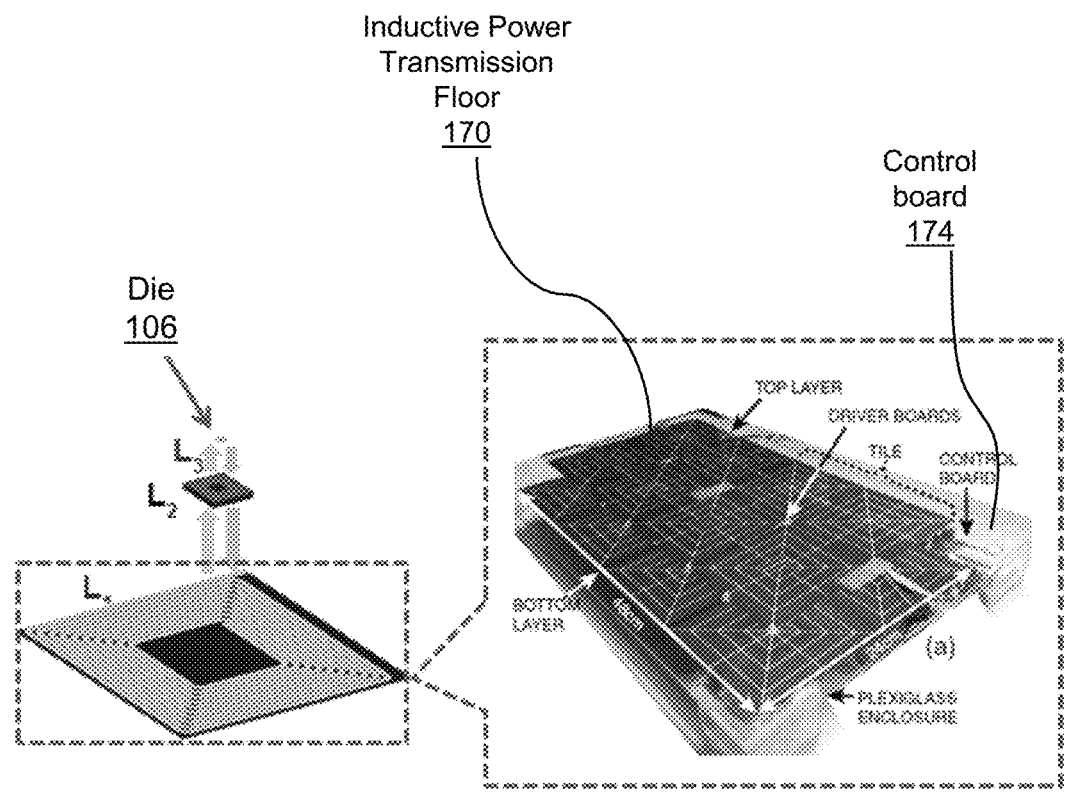
FIG. 7 shows an embodiment of a base station for a system for in situ electrochemical imaging comprising an inductive power transmission floor.
Figure 8:
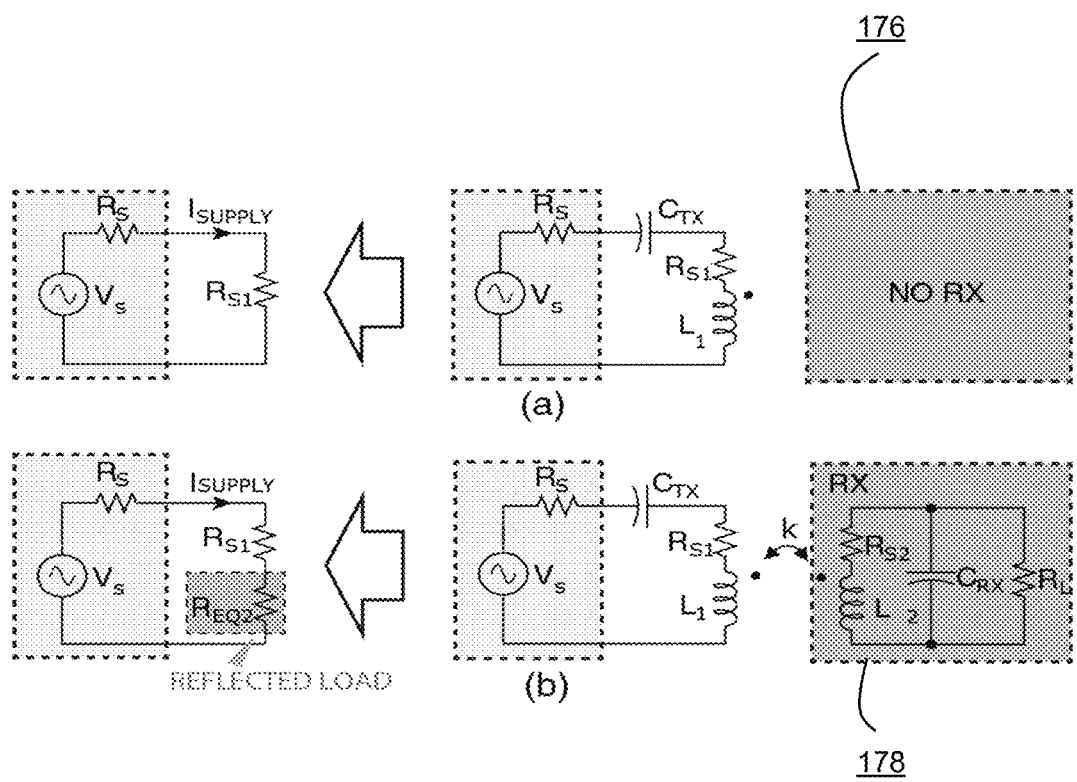
FIG. 8 shows a circuit for dynamic load tracking using reflected impedance monitoring for the embodiment of the base station.
Figure 9:
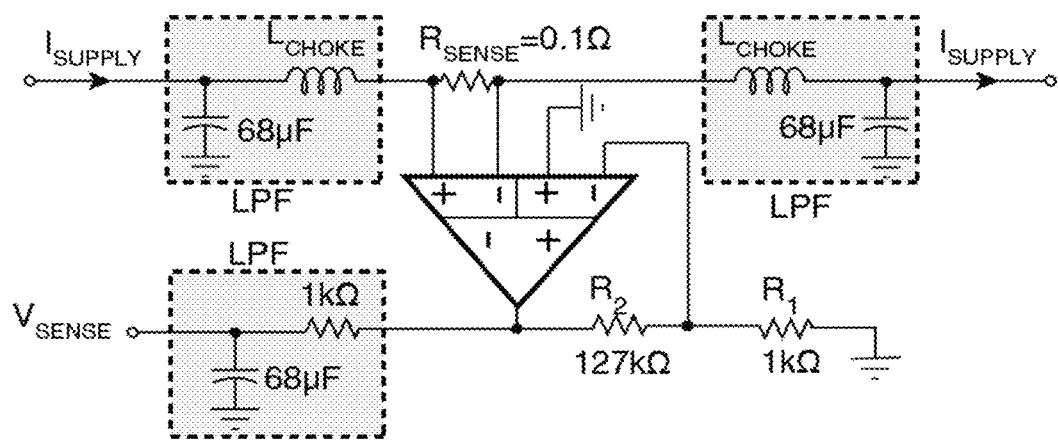
FIG. 9 shows an implementation of a differential amplifier circuit for dynamic load tracking for the embodiment of the base station.

Referring now to FIGS. 7 to 9, shown therein is a particular embodiment of the base station 102 providing an inductive power transmission floor 170 comprising an array of individual transmitting coils 120 and associated components developed on two-layer printed circuit board, configured and driven by a control board 174. The base station also comprises receivers 126 (e.g., a separate USB dongle). The inductive power transmission floor 170 provides power to the receiver device 104 and the die 106, such as an implanted die for K+ imaging. The floor 170 comprises an array of planar inductive transmitting coils 120 which may be located at the bottom of an environment housing a subject 112, an example of such an environment being the cage of an animal, to be tested with a die 106. The subject 112 can be dynamically tracked by an impedance sensing circuit in the control board 174 of the powering system. The impedance sensing circuit can continuously measure the impedance of each coil to determine whether a receiver device 104 is present. Once the power receiver is located, it may be powered by a coil closest to the receiver device 104. FIG. 8 illustrates a circuit for dynamic load tracking using reflected impedance monitoring as described above. Element 176 illustrates the circuit diagram when a receiver device 104 is not present in proximity to the transmission floor 170. Element 178 illustrates the circuit diagram when a receiver is present in proximity to the transmission floor 170, and the receiver's associated reflected load. FIG. 9 illustrates an implementation of a differential amplifier circuit for monitoring the supply voltage to measure the reflected impedance of the receiver.

Figure 10:
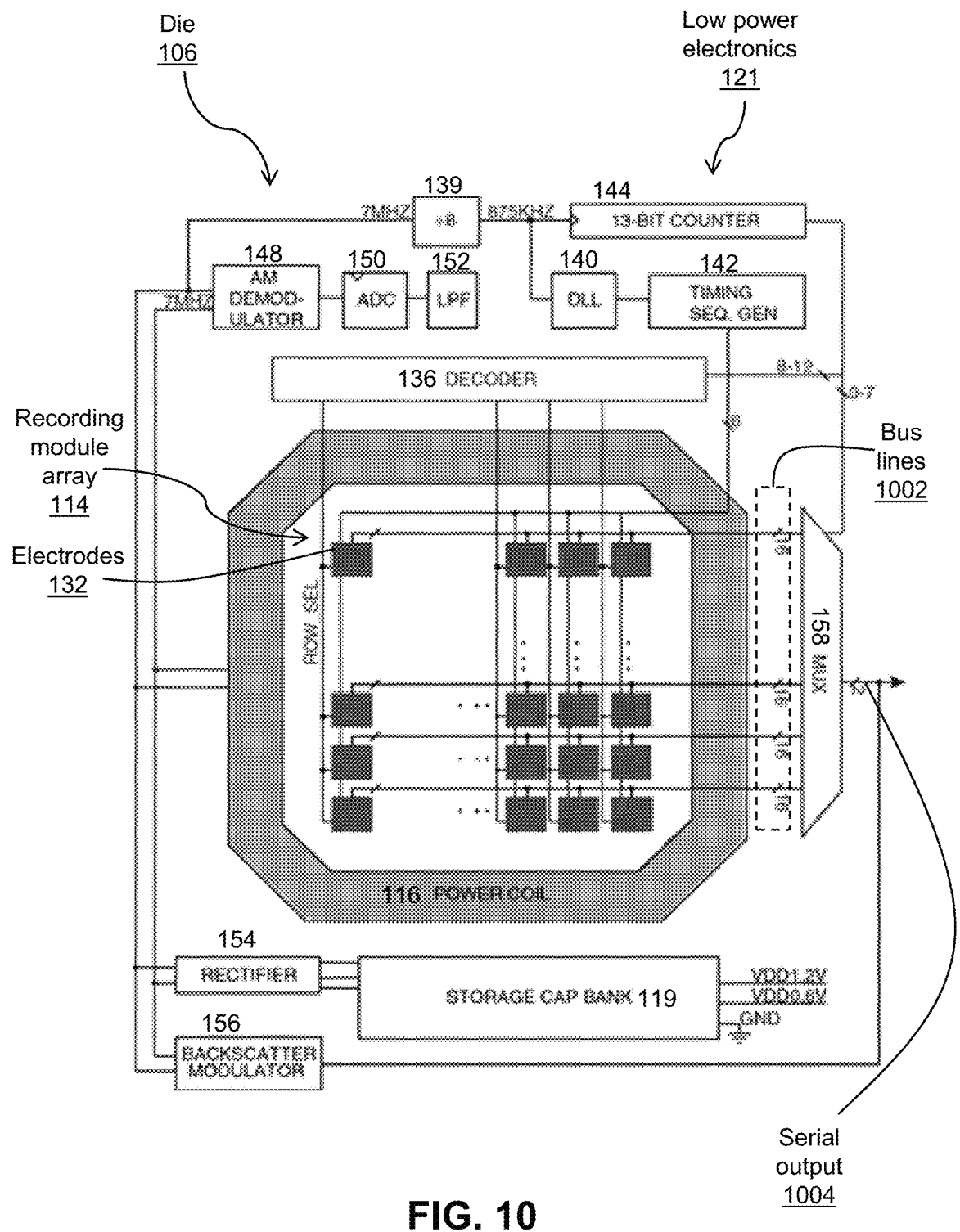
FIG. 10 shows a schematic level representation of a die for in situ electrochemical imaging.
Figure 11:
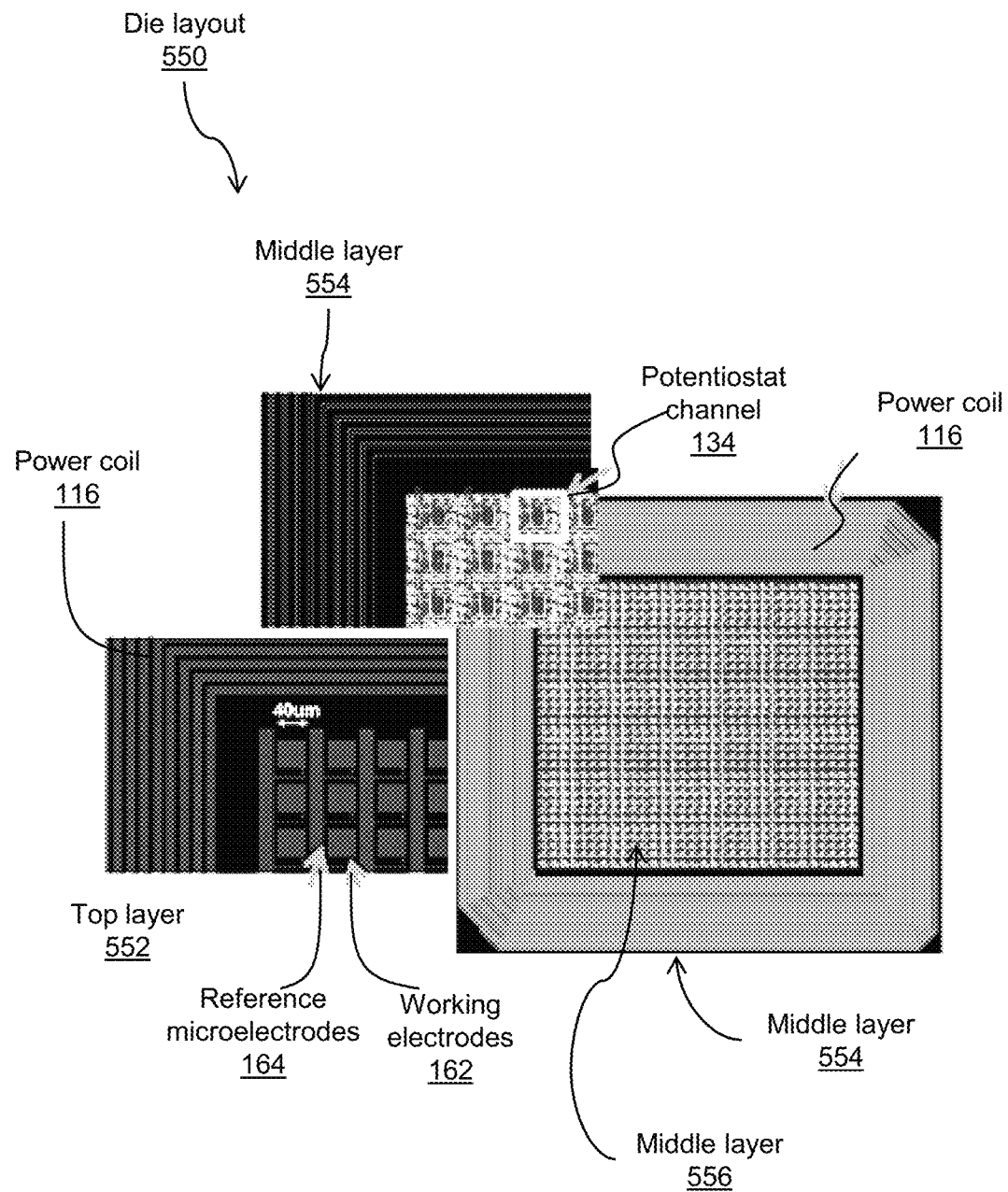
FIG. 11 shows a layout level representation of a die for in situ electrochemical imaging.
Figure 12:
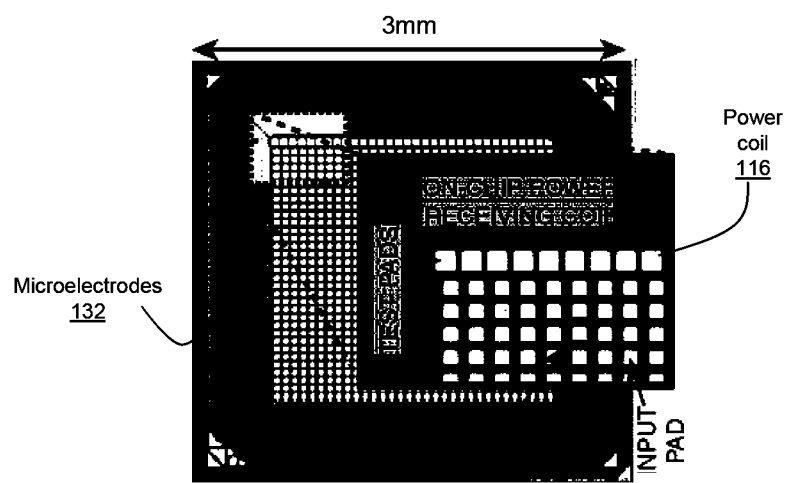
FIG. 12 shows a fabricated die micrograph level representation of a die for in situ electrochemical imaging.

Referring now to FIGS. 10 to 12, shown therein are illustrations of the die 106 at the schematic level (FIG. 10), layout-level (FIG. 11), and fabricated die micrograph level (FIG. 12). The configuration of the components of the die 106 and particularly the lower-power electronics 121 for providing the functionality described above will now be described in additional detail with respect to FIGS. 10 to 12.

As described above, the die 106 comprises a recording module array 114 comprising an array of electrodes 132, such as a 32×32 array, with a dedicated digital potentiostat channel 134 fabricated underneath each electrode (illustrated in FIG. 11, 13). The energy harvesting power coil 116 is fabricated around the electrode array. Low-power electronics 121 comprising components for peripheral clock generation and data processing, as well as power management circuits are fabricated around the potentiostat channel 134 array, underneath the energy harvesting coil 116. More particularly, the low-power electronics 121 in FIG. 10 are shown to comprise a delay-locked loop ("DLL") 140, a timing sequence generator 142, a 13-bit counter 144, a divide-by-8 frequency divider 139, a decoder 146, an amplitude-modulated demodulator ("AM Demodulator") 148, an analog to digital converter ("ADC") 150, a low-pass filter ("LPF") 152, a rectifier 154, a backscatter modulator 156 and a multiplexer 158, the functionality of which will be described below. A storage capacitor bank 119 is also shown.

Referring now to FIG. 10 and describing in more detail the operation of a particular embodiment of the die 106, once the die is activated at block 204 of method 220, the potentiostat channels 134 of the recording module array 114 periodically record the electric charge accumulation on their corresponding microelectrode 132 and convert them to digital data, such as 16-bit digital words which can be stored in 16 D-flip-flops (not shown) fabricated inside each channel. After each conversion, the 16-bit content of all the channels may be extracted and serialized by a readout circuit (embodied in FIG. 10 by column decoder 136 and row multiplexer 158) The column decoder 136 illustrated above the array switches the content of the channels along each column onto the 16-bit bus lines 1002 running along the rows of the array. The multiplexer 158 sequentially reads out the row buses once they are switched onto the D-flip-flops inside the individual channels along the selected column. The multiplexer produces two serial outputs 1004 corresponding to the less significant and the more significant bytes of channels' 134 data words. The serial outputs of the multiplexer are fed into the on-chip radio transmitter 156 which sends the data out to the base station 102 (in the two-stage system), or the intermediate stage 104 (in the three-stage system).

With respect to the power management circuit of electronics 121, electric energy to power the die 106 microsystem in FIG. 10 may be generated by an integrated rectifier 154 which can convert AC voltage induced in the energy harvesting coil 116 into supply voltages, such as at 0.6V and 1.2V. Optionally, the 0.6V voltage may be used to power the all the digital circuits and the 1.2V supply can be used to power the analog signal processing and the RF front-end data communication circuits.

With respect to the clock generation of electronics 121, all the global clock, control and timing sequence signals may be generated from the alternating signal induced into the energy harvesting coil 116 using the clock generation blocks 148, 150. An illustrative 6.7 MHz signal of the coil 116 may be converted to a preferred global clock, such as an 875 kHz global clock by a frequency divider, such as a divide-by-8 frequency divider 139. The global clock may then then used by 13-bit counter 144 to generate all the 13-bit control signals for the MUX 158 and the decoder 136 in the readout circuit, as well as the 6 timing sequence signals used to run the individual digital potentiostat channels 134.

Referring now to FIG. 11, shown therein is an embodiment of the layout 550 of the CMOS die 106. On the top layer 552, the coil 116 is laid out around the periphery of the chip while the core of the chip is populated with the microelectrodes 132 comprising working electrodes 162 ("WE") realized by 40 um×40 um aluminum pads on the top interconnect layer of the chip, as well as a long common reference microelectrode 164 ("RE") which occupies the space in between the individual microelectrodes 132 and creates a two-electrode electrochemistry cell (i.e. working+reference electrodes) with each individual charge-sensing microelectrode. Underneath each individual microelectrode pad, as shown in middle layers (e.g., there may be, for example, 10 layers below top layer which are included in 554 and 556), there is a densely laid-out digital potentiostat channel 134 which transduces the charge on the aluminum pad above it. Element 554 provides an enlarged view of the middle layer 556.

Referring now to FIG. 12, shown therein is a micrograph of the fabricated CMOS die, according to a particular embodiment. The microelectrode array 132 and the energy harvesting coil 116 can be seen on the top level. There is an additional layer of auxiliary pads 166 directly above the microelectrode array which may be used for testing and fault finding purposes.

Figure 13:
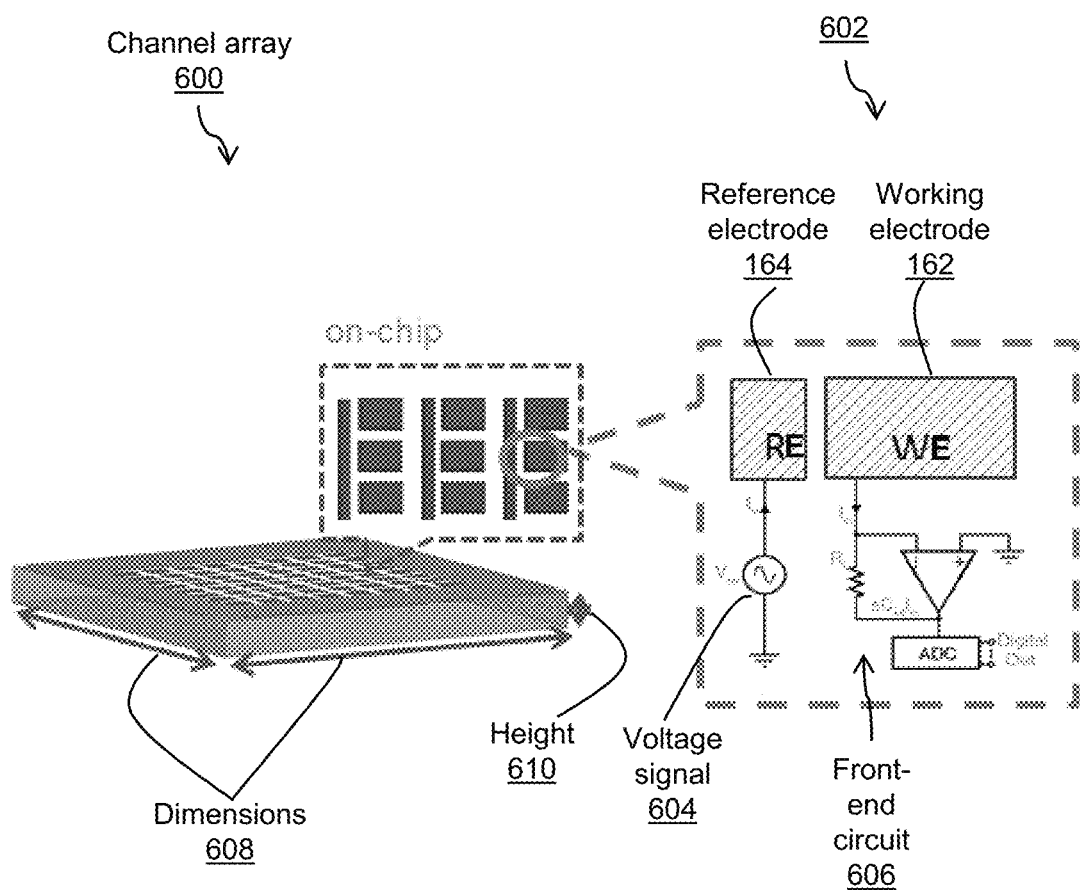
FIG. 13 shows an embodiment of an amperometric channel array of a die for in situ electrochemical imaging.

Referring now to FIG. 13, shown therein is an embodiment 600 of the amperometric channel array 134 for the die 106. The amperometric recording channels 134 are organized in the form of an array in the center of the die underneath the electrodes 132. The area is surrounded on the top layer by the power coil 116. The die may measure approximately 3 mm along dimensions 608, and 0.3 mm along its height 610. With regards to the electrodes 132, each column comprises 32 working electrodes 162 and one reference electrode 164 running along the side of the entire column. During amperometry, the reference electrode 164 is driven by a periodic voltage signal (sinusoid, ramp, or sawtooth) 604 while voltage of all the working electrodes 162 are held at a constant value (of approximately 300 mV to 500 mV). During operation, as shown in the diagram 602, the current flowing into the WE 162 as a result of its potential difference with the RE 164 is recorded by a front-end circuit 606 operating essentially as a transimpedance amplifier. The output of the transimpedance amplifier circuit 606 may be converted to digital words read by the array readout circuit after in-channel bandpass filtering.

Based on the embodiments of the die 106 described above, and the associated operational values for the components therein (particularly as described and illustrated in FIGS. 10 to 13), an approximately thousand channel implant die 106 may have approximately 0.08 uW power budget per channel 134 for use with amperometry (such as K+ amperometry), analog-to-digital-conversion and digital bandpass-filtering—which come up to approximately 100 uW in total power consumption for the die when including the power required for clock and bus generation and distribution circuits and data telemetry. Based on known values, a straightforward block-by-block implementation of the transimpedance amplifier, ADC, and digital bandpass filter will not meet the low-power, high-sensitivity, and small-size requirements of the in vivo K+ imaging system proposed here. The embodiments described below with reference to FIGS. 14 to 35 may meet some performance requirements by minimizing size and power consumption of each channel by merging circuit blocks and simplifying the resulting schematic based on the known properties of the expected channel input signal.

Figure 14:
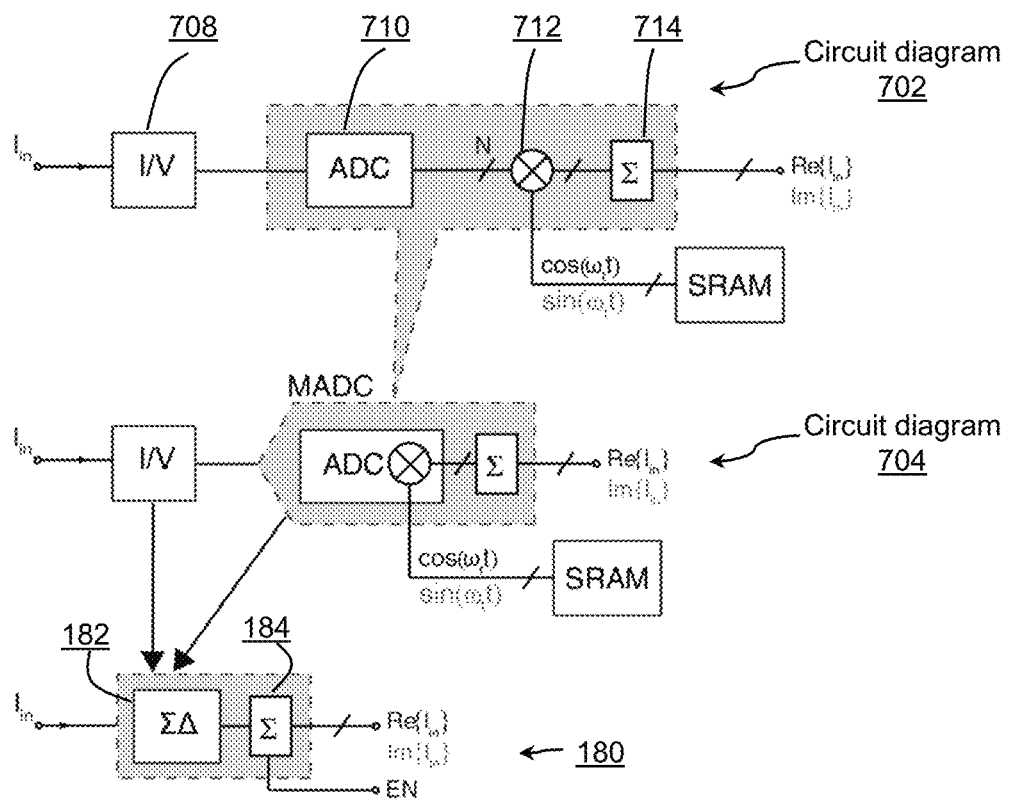
FIG. 14 shows circuit diagrams of an amperometric channel minimized in size and power consumption by merging circuit blocks.

Referring to FIG. 14, shown therein are amperometric channel circuit diagrams. Embodiment 702 illustrates a conventional block diagram of an amperometric channel comprising a transimpedance amplifier 708 ("TIA") (current "I" to voltage "V" converter), an ADC 710, a digital multiplication 712 and an accumulation circuit (counter) 714. Depending on the digital coefficient used, the output of the counter will represent the real or imaginary part of the input current with respect to the applied voltage signal at the reference. Embodiment 704 illustrates the block diagram of a simplified channel 134 where the size and power consumption have been reduced by performing a coefficient multiplication operation during the ADC operation in the mixed-signal domain.

The channel diagrammed at element 180 provides a further minimization of the amperometric channel using a delta-sigma front-end ADC, which may have significantly reduced size and power consumption. As compared with embodiment 704, in embodiment 180 the transimpedance stage has been incorporated into the ADC in block 182. By implementing the ADC in a delta-sigma topology, the front-end integrator is tasked with I-to-V conversion. The size and power requirements of the ADC itself may be further minimized by removing the front-end op-amp from a conventional implementation of the ADC and performing integration by a grounded capacitor, as described below. Further minimization of the size and power requirements of the circuit components may be achieved by approximating the multiplication coefficients by a single bit approximation of those values at block 184. As will be described below, in particular circumstances, this approximation may not significantly impact the outcome of the amperometry due to the particular frequency spectrum of the input signal.

In the following, particular implementations of the amperometric channel 180 and blocks 182 and 184 will be described. Further, the validity of the proposed minimization steps (i.e. removing the front-end op-amp and providing 1-bit coefficient approximation) will be set out.

Figure 15:
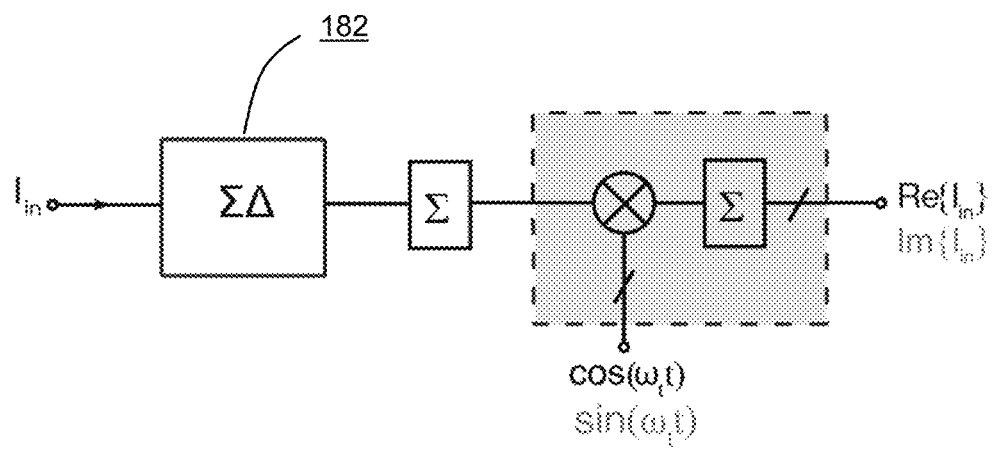
FIG. 15 shows a block diagram of an amperometric channel implemented by a delta-sigma front-end ADC.
Figure 16:
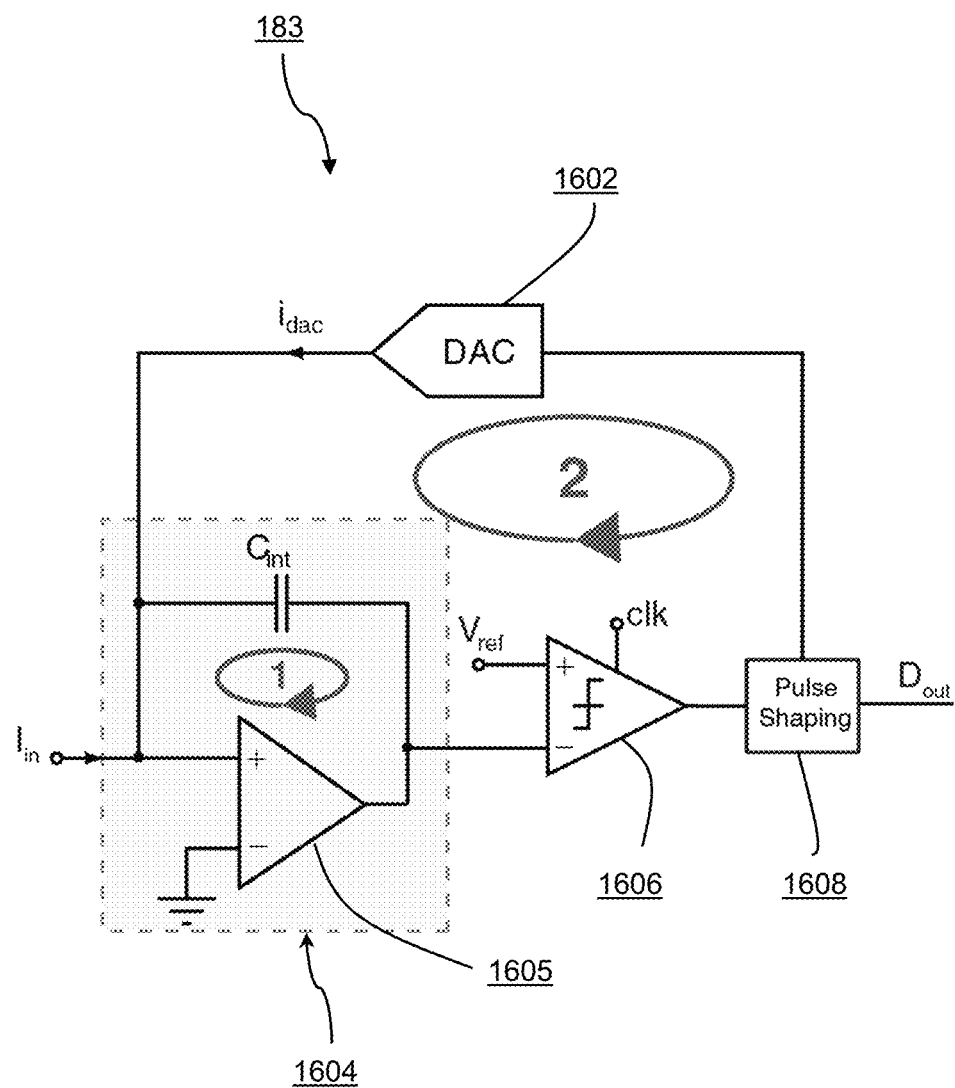
FIG. 16 shows a conventional implementation of a typical first order ADC used for amperometry.
Figure 17:
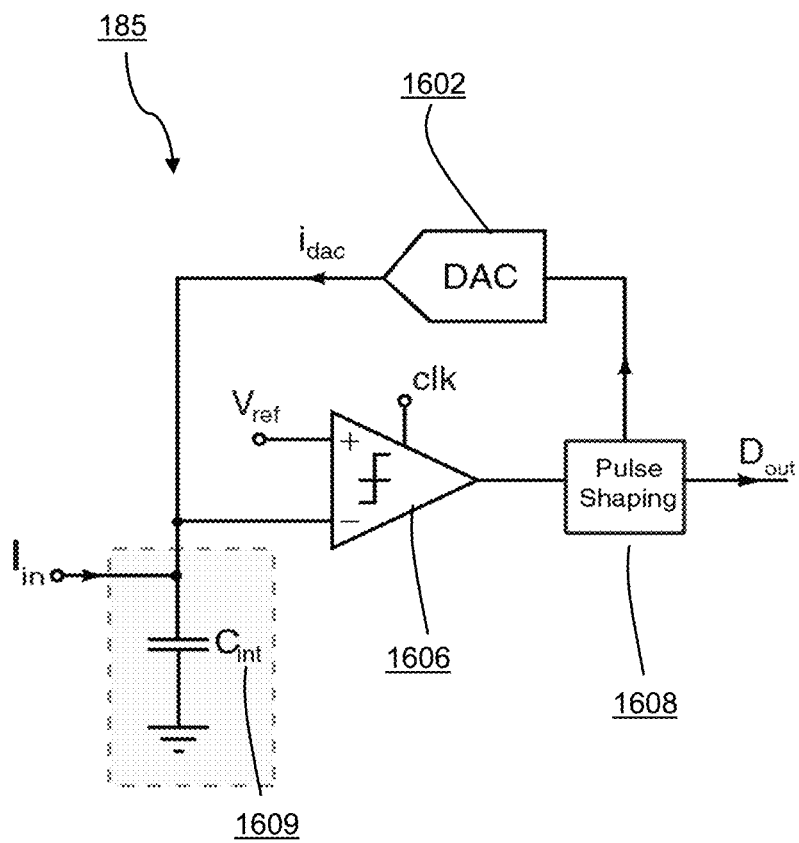
FIG. 17 shows an op-amp-less delta-sigma ADC.

Referring now to FIG. 15, shown therein is a block diagram of the amperometric channel 180 implemented by a delta-sigma front-end ADC 182. FIG. 16 illustrates a conventional implementation of a typical first order ADC used for amperometry 183 comprising a digital-to-analog converter ("DAC") 1602, an integrator circuit 1604 comprising an op-amp 1605 and a capacitor $C_{int}$, an op-amp 1606 and a pulse shaping block 1608. A negative feedback loop (loop 1) in the integrator 1604 creates a virtual ground at the input terminal of the ADC. Another negative feedback loop in the circuit of FIG. 16 similarly works toward making a virtual ground at input (loop 2) by keeping integrator output as close to Vref as possible. FIG. 17 illustrates an op-amp-less delta-sigma ADC 185 resulting by removing loop 1 from the conventional implementation in FIG. 16 and providing a grounded capacitor 1609. Performance of op-amp-less delta-sigma ADC in keeping a virtual ground at the input node improves by increasing the oversampling frequency and reducing the DAC coefficient.

The validity of the embodiment of the op-amp-less ADC 185 described above will now be discussed with reference to FIGS. 18 to 26.

Figure 18:
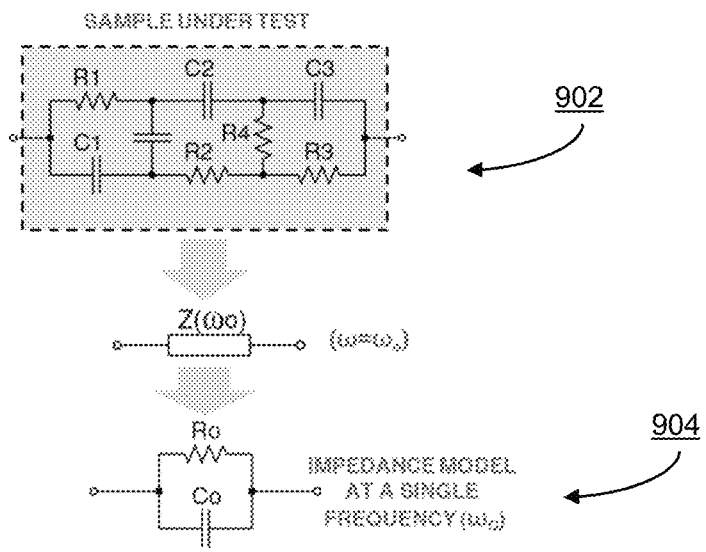
FIG. 18 shows a lumped model of an arbitrary passive medium under-test.

In order for the op-amp-less potentiostat 185 shown in FIG. 17 to produce valid electrochemical measurement results, it should function approximately equivalently to the ideal circuit 183 in FIG. 16. Specifically, to conduct the electrochemical measurement shown in FIG. 13 in diagram 602, the potentiostat circuit should accurately compute the electrical impedance between the working 162 and the reference electrode 164 at a known test frequency. FIG. 18 illustrates the lumped model of an arbitrary passive medium under-test. While the lumped RC model of the medium may comprise an arbitrarily complex network 902 of resistor ("R") and capacitor ("C") components, at a single known frequency, the medium is accurately modeled by an equivalent parallel network 904 of one R (Ro) and one C (Co). The mathematical equivalency of the complex lumped model to the simplified parallel RoCo network at the known test frequency of ωo is provided below. The goal of measurement using potentiostat is to accurately determine the values of $R_o$ and $C_o$ at the test frequency $\omega_o$.

$$Z(\omega_0) = \text{Re}\{Z(\omega_0)\} + j\text{Im}\{Z(\omega_0)\}$$

$$= \underbrace{\text{Re}\{Z(\omega_0)\}}_{R_0} + j\omega_o \underbrace{\text{Im}\{Z(\omega_0)\}/\omega_0}_{C_0}$$

$$Z(\omega_0) = R_0 + j\omega_0 C_0$$

Figure 19:
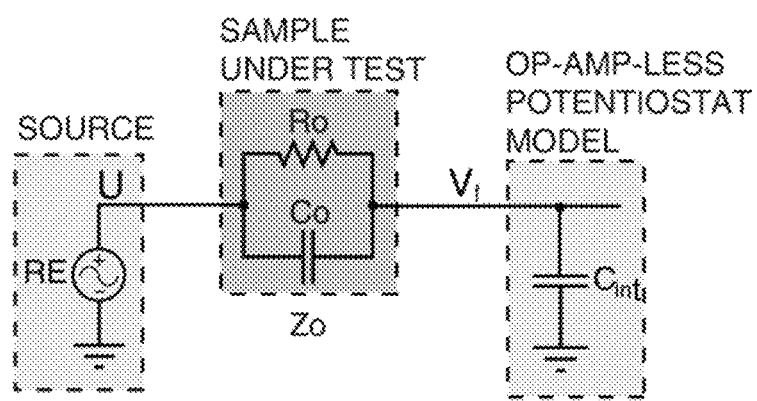
FIG. 19 shows a transient lumped RC model of the sample under test by an op-amp-less potentiostat.
Figure 20:
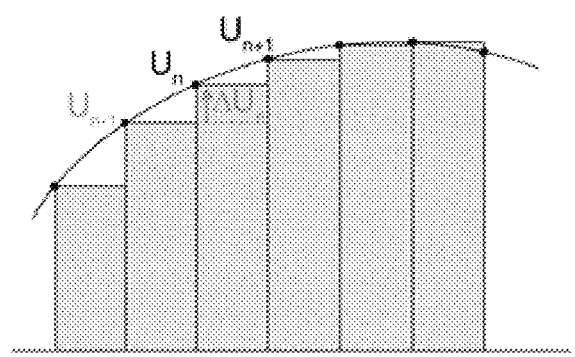
FIG. 20 shows a discrete-time approximation of a source voltage signal in the model of FIGS. 18 to 19.
Figure 21:
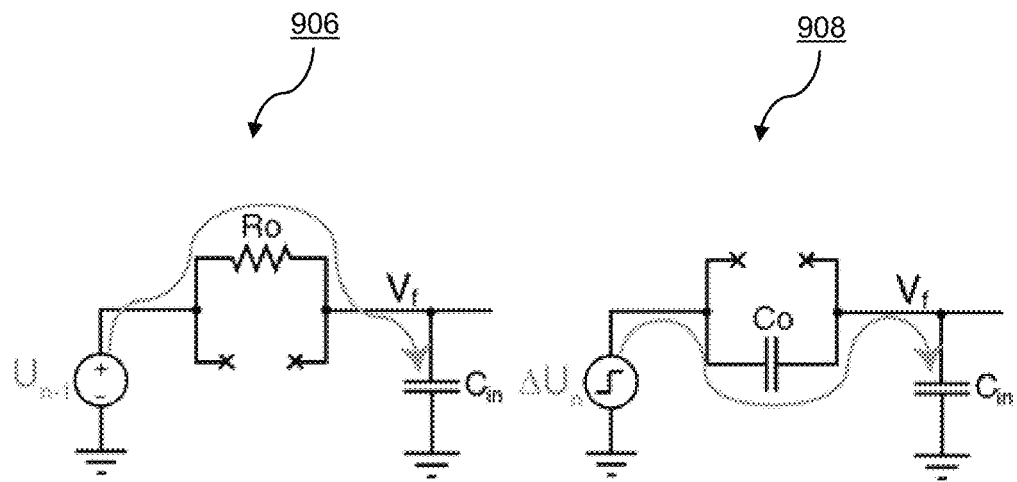
FIG. 21 shows the decomposition of a source signal of FIGS. 18 to 20 into constant voltage and step signal components.

FIG. 19 illustrates the transient lumped RC model of the medium under test by the op-amp-less potentiostat 185 in FIG. 17 during the time between two consecutive sampling instances. As illustrated, during the time between two consecutive samples, the test on the medium only results in a change in the integration capacitance Cant of the potentiostat because all the active components of the potentiostat are off during the relevant time. Based on this model, the current entering the potentiostat, caused by applying the voltage U to the sample, creates a change in the input potential $V_f$. The relationship between $V_f$ and the sample under test can be determined by approximating the continuous-time output of the source U with its discrete-time equivalent values U(n−1), U(n), U(n+1), . . . as shown in FIG. 20, providing a discrete-time approximation of the source voltage signal. Similarly, the value of other signals can be denoted as the (n−1)th, nth, (n+1)th, . . . sampling instances using (n−1), (n), (n+1), indices respectively. With this approximation, U remains constant and equal to U(n−1) until the next sampling instance. Upon the nth sampling instance, an ideal step signal, ΔU(n), suddenly raises the level of U to its next discrete level, U(n). By this approximation, the change in Vf between the (n−1)th and nth samples is quantified by superimposing the outcomes of the two half-circuits shown in FIG. 21, half-circuit 906 representing the constant signal U(n−1) and half-circuit 908 the ideal step signal ΔU(n) at the end of the interval. Accordingly, FIG. 21 illustrates the decomposition of the source signal into constant voltage and step signal components. The constant voltage U(n−1) creates a current through R0 while the C0 blocks the constant U(n−1) entirely. Conversely, the ideal step voltage ΔU(n) changes Vf through C0 instantly at the nth sampling moment but, at the same instant, is blocked by Ro entirely.

Figure 22:
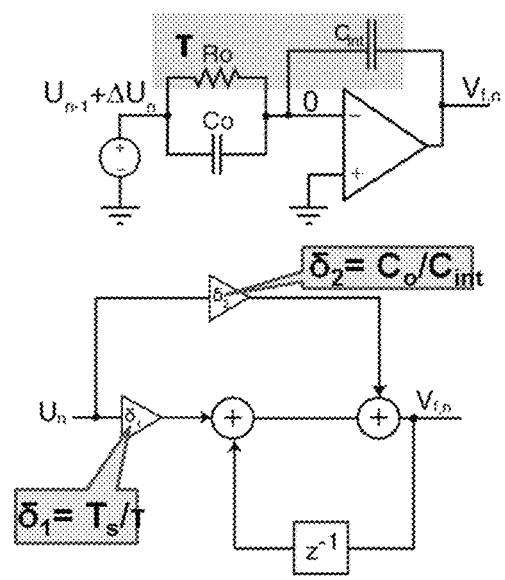
FIG. 22 shows a z-domain model of an ideal integrator in a conventional ΔΣ-ADC-based potentiostat.
Figure 23:
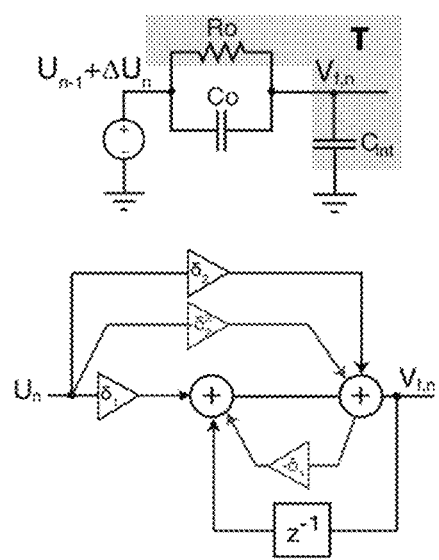
FIG. 23 shows a z-domain model of an integrator for an op-amp-less potentiostat.
Figure 24:
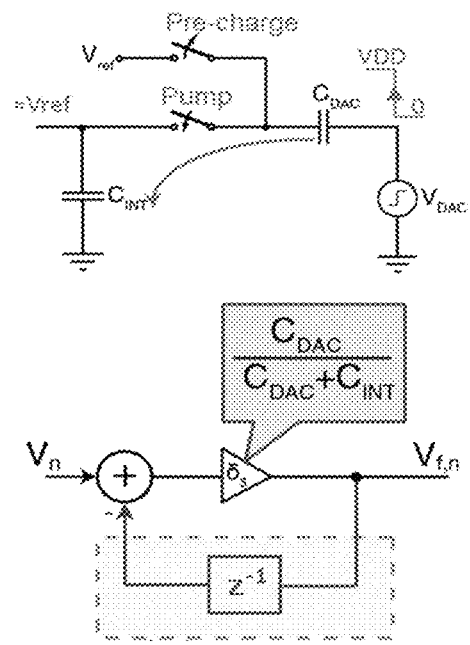
FIG. 24 shows a z-domain model of a 1-bit DAC in the op-amp-less circuit.

FIG. 22 illustrates the z-domain model of the ideal integrator in a conventional ΔΣ-ADC-based potentiostat, as shown in FIG. 16, based on the discrete-time approximation shown in FIG. 20. The values of the coefficients δ2 and δ1 in this model are determined by the values of C0 and the sample time constant τ=R0C0, respectively. FIG. 23 shows the derivation of the same model for the integrator in the op-amp-less potentiostat 185 in FIG. 17. As shown, removing the op-amp causes two additional branches with the weights δ2 and δ1 to appear in the z-domain model of the potentiostat. FIG. 24 shows the z-domain model of the 1-bit DAC in the op-amp-less potentiostat 185 of FIG. 17. As illustrated, an unwanted branch appears between the DAC output, Vf, and its input, V(n), when there is no op-amp in the integrator.

Figure 25:
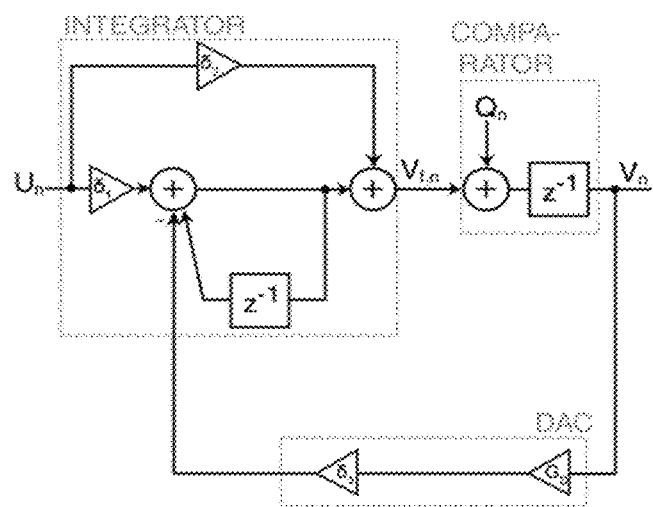
FIG. 25 shows an ideal whole system model for a $\Delta\Sigma$-ADC-based potentiostats.
Figure 26:
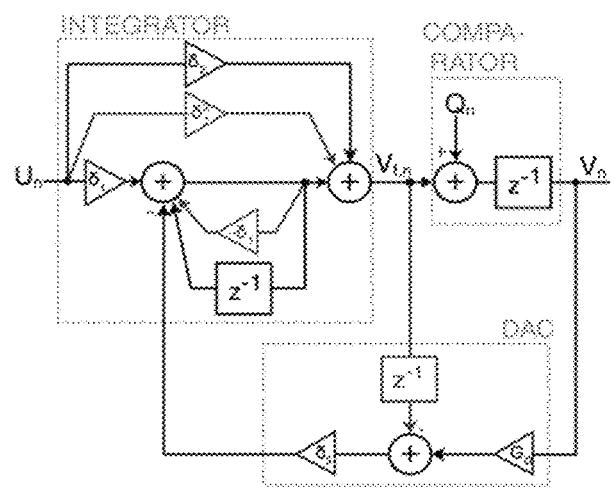
FIG. 26 shows an op-amp less whole system model for a $\Delta\Sigma$-ADC-based potentiostats.

FIGS. 25 and 26 illustrate the whole system models of the ideal and op-amp-less ΔΣ-ADC-based potentiostats of FIG. 16 and FIG. 17, 183, 185, respectively. The whole-system models are derived by adding the quantizer block to the z-domain integrator and models in FIGS. 22 and 23, and 24, respectively.

The derivation of the whole-system z-domain transfer functions of the conventional ΔΣ-ADC-based potentiostats 183 of FIG. 16 may be as follows:

$$\frac{V_n}{Z^{-1}} = \left(\delta_2 + \frac{\delta_1}{1-Z^{-1}}\right)U_n - \frac{G_D\delta_3}{C_{DAC}+C_{INT}}V_n$$

$$\frac{V_n}{U_n} = \frac{\delta_2(1-Z^{-1})+\delta_1}{1-Z^{-1}+G_D\delta_3 Z^{-1}}Z^{-1}$$

$Sel.LSB(U_n)$ s.t. $G_D\delta_3 = 1$

THEN $V_{n+1} = [\delta_2(1-Z^{-1})+\delta_1]U_n$ $U = U_m\cos\omega_0 t$ $$V = \frac{2\pi U_m}{j\omega_{clk}C_{int}}\left[\frac{1}{\underbrace{\frac{R_0}{Re\{\frac{1}{Z_0}\}}}}\cos\omega_0 t + \underbrace{j\omega_0 C_0\sin\omega_0 t}_{Im\{\frac{1}{Z_0}\}}\right]U_n$$

The derivation of the whole-system z-domain transfer functions of the op-amp-less ΔΣ-ADC-based potentiostat 185 of FIG. 17 may be as follows:

$$\frac{V_n}{Z^{-1}} = \left[\delta_2(1-\delta_2) + \frac{\delta_1 - \delta_2(1-\delta_2)\delta_3}{1+\delta_1-(1-\delta_3)Z^{-1}}\right]U_n - \frac{\delta_1 - \delta_2(1-\delta_2)\delta_3}{1+\delta_1-(1-\delta_3)Z^{-1}}V_n$$

IF: $\delta_1 \ll 1, \delta_2 \ll 1, \delta_3 \ll 1$

AND $Sel. LSB(U_n)$ s.t. $G_D\delta_3 = 1$

THEN $V_{n+1} = [\delta_2(1-Z^{-1})+\delta_1]U_n$, $U = U_m\cos\omega_0 t$ $$V = \frac{2\pi U_m}{j\omega_{clk}C_{int}}[\underbrace{\frac{1}{\frac{R_0}{Re\{\frac{1}{Z_0}\}}}}\cos\omega_0 t + \underbrace{j\omega_0 C_0\sin\omega_0 t}_{Im\{\frac{1}{Z_0}\}}]U_n$$

Based on the derived z-domain transfer functions of the conventional and op-amp-less potentiostat circuits above, the op-amp-less design may be approximately equivalent to the ideal design under the some conditions, such as if: (1) parallel capacitive component of the medium $C_o$ being tested is much smaller than the integrating capacitance $C_{int}$, (2) the bandwidth of the combination of the medium and the integrating capacitor $C_{int}$ ($1/R_oC_{int}$) is much less than the sampling frequency ($f_s$ or $1/T_s$), and (3) the admittance of the medium under test is much less than the equivalent conductance of the I-DAC at the sampling frequency.

$\delta_1 \ll 1$ $C_o \ll C_{int}$: SMALL ELECTRODES $\delta_2 \ll 1$ $R_oC_o \ll T_S$: HIGH OSR $\delta_3 \ll 1 G_d \ll 1$: SMALL CURRENTS In the context of some embodiments of the die and associated amperometry channel configurations described above, the condition (1) may be met due to the small size of the working electrodes (40 μm) which may cause the medium capacitance to be effectively equal to the fringe capacitance between the WE and the adjacent RE in the top layer (MA) layout 552 of FIG. 11, while $C_{int}$ is the MIM capacitor with approximately the same size as WE implemented underneath it on the E1 layer. Condition (2) may be met by designing the ADC to work at sampling ratios as high as 100 MHz while medium frequency is limited to few kHz. Condition (3) may be met because of high oversampling and can be further improved by used a higher voltage DAC using the 3.3V devices in available in the IBM 0.13 μm standard process.

Referring now to FIG. 27 to FIG. 30, shown therein are embodiments approximating the multiplication coefficients by a single bit approximation of those values at block 184 of channel embodiment 180.

Figure 27:
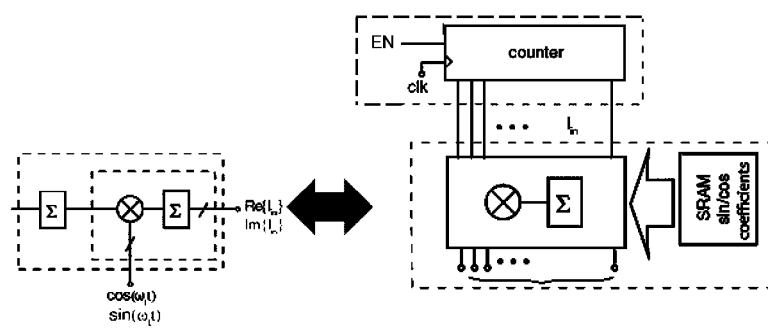
FIG. 27 shows an implementation of a digital multiplication operation performed on the output of a delta sigma ADC after a decimation filter.

FIG. 27 shows a conventional implementation of a digital multiplication operation performed on the output of a delta sigma ADC after a decimation filter, i.e. particularly a conventional implementation of the sine and cosine waveform multiplication at ADC output. The digital coefficients are stored in memory and applied in a multibit MAC operation which requires SRAM storage, routing of a parallel bus of sin/cos coefficients to each amperometry channel, and implementation of a complete 16-bit MAC operation inside each channel.

Figure 28:
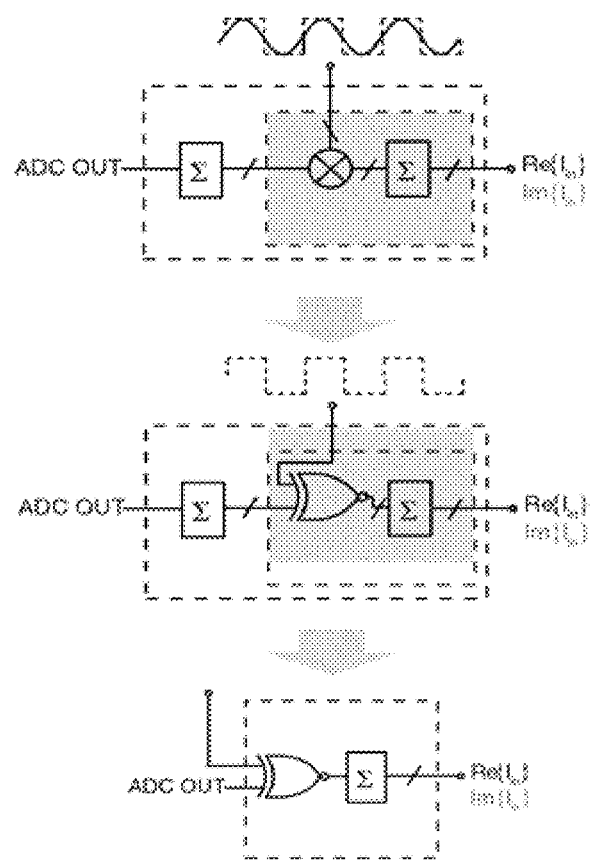
FIG. 28 shows the replacement of the 16-bit coefficient multiplication by a 1-bit XOR.

FIG. 28 illustrates the replacement of the 16-bit coefficient multiplication by a 1-bit XOR according for block 184 of embodiment 180. By approximating the sinewave (and cosine waveforms) by a squarewave of the same frequency and phase, the multi-bit multiplication of the output of the first counter may be minimized by being replaced by a multi-bit XOR operation between the squarewave and the digital word at the output of the first counter. As the output of the first counter is reset periodically (to represent a low-pass filter), the first counter is eliminated by moving the XOR operation to the front and merging the two counters (the reset and the non-reset counters). Therefore the 16-bit digital coefficient multiplication and accumulation is replaced by a 1-bit XOR and a 1-bit counting operation.

Figure 29:
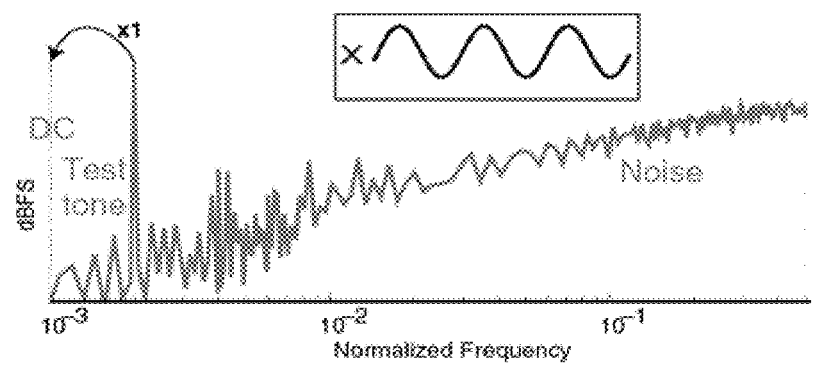
FIG. 29 illustrates decibels relative to full scale ("dbFS") against frequency for a tone signal after down-conversion by an ideal sine wave signal.
Figure 30:
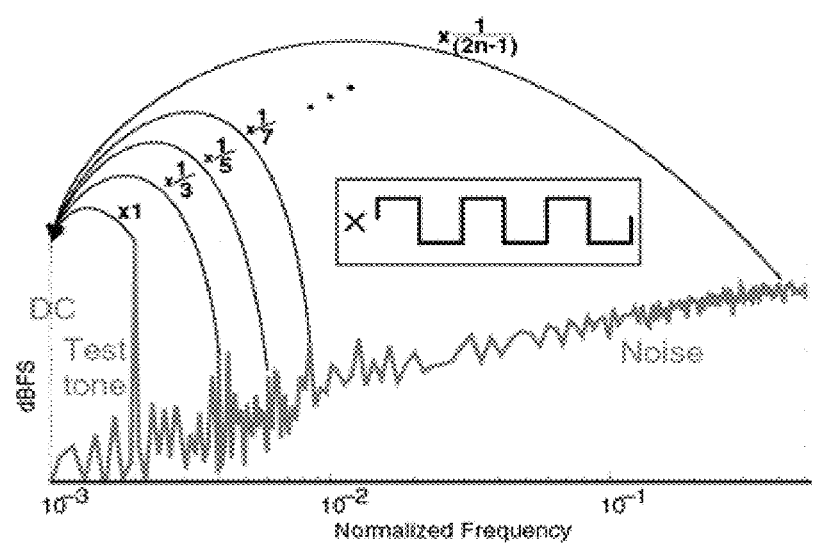
FIG. 30 illustrates dbFS against frequency for a tone signal after down-conversion by a squarewave approximation of a sinewave signal.

FIGS. 29 and 30 illustrate possible representations of decibels relative to full scale ("dbFS") against frequency for down-conversion of a signal by an ideal sine wave and a squarewave approximation, respectively. As shown in FIG. 29, multiplying the output of the sigma delta ADC by a high-resolution multibit-sinewave down-converts the target component of the ADC output spectrum to DC which is the value stored in the second counter. However, as shown in FIG. 30, the squarewave multiplication may also downconvert all the noise components occurring at the higher-order harmonics of the sinewave frequency. However, due to the noise-shaping property of the delta-sigma ADC, the down-conversion of the noise spectrum components may not corrupt the final output as the noise components folded down to DC by the first few harmonics may be minimal as compared to the signal component. As the noise components start to grow for higher harmonics, the weight of the higher order harmonics start to drop by a function of the same or more strength. Therefore, the noise shaping property of the delta-sigma ADC may effectively suppress the impact of the higher order harmonics of the squarewave during the proposed 1-bit multiplication.

Figure 31:
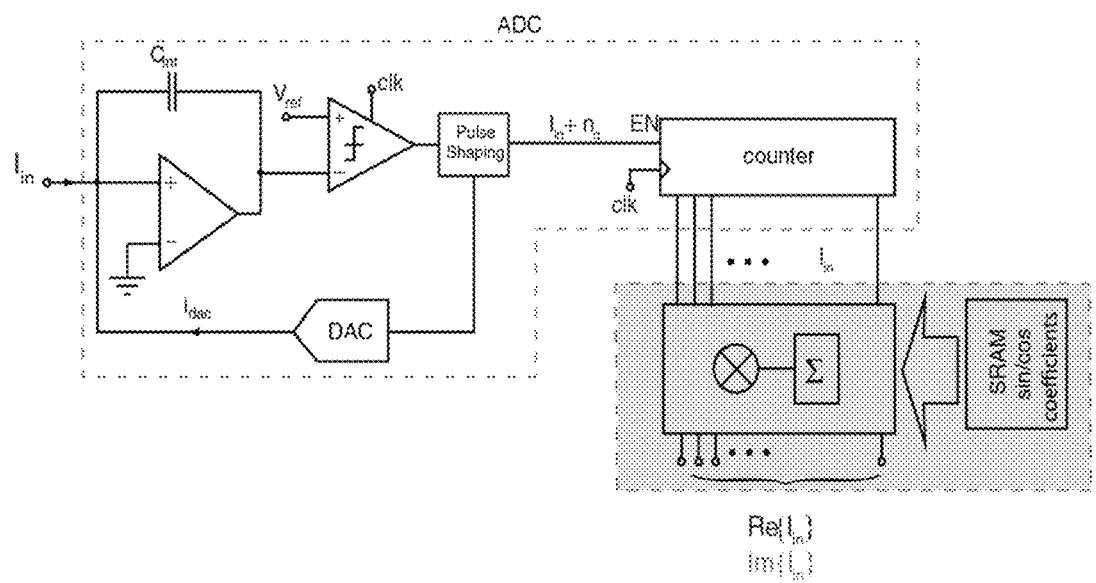
FIG. 31 shows schematic diagrams of an amperometric channel implemented by conventional circuit blocks.
Figure 32:
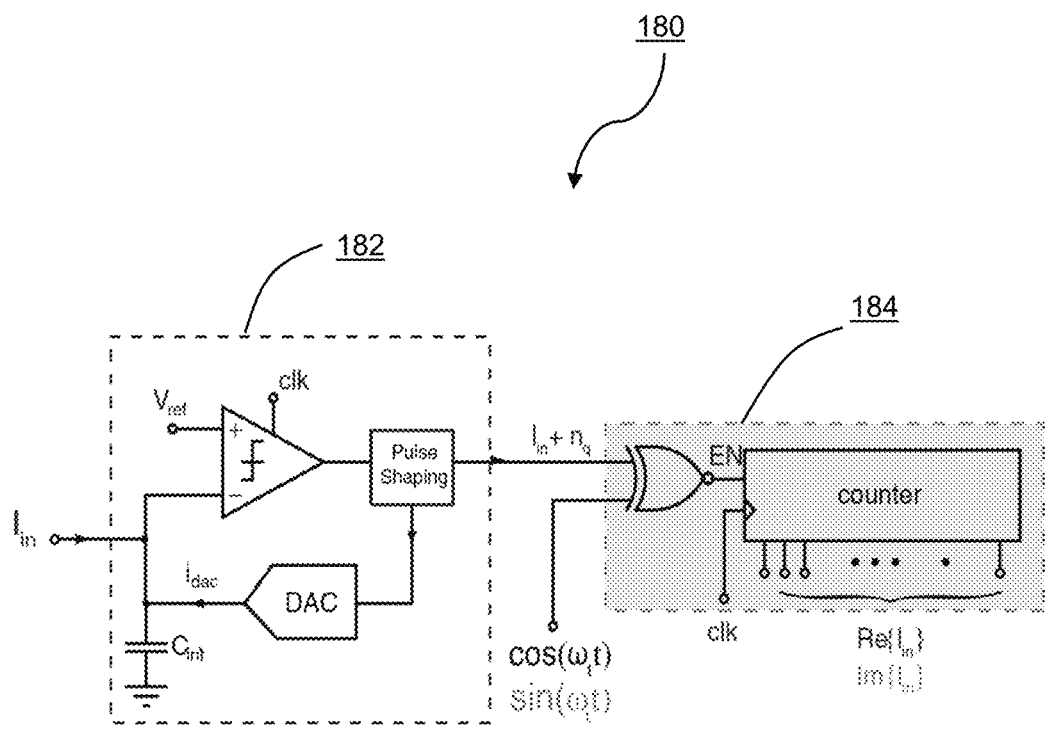
FIG. 32 shows schematic diagrams of an amperometric channel according to a power- and area-minimized implementation.

Referring now to FIGS. 31 to 32, shown therein are schematic diagrams of amperometric channels implemented by conventional circuit blocks in FIG. 31, and, in FIG. 32, a power- and area-minimized implementation of the amperometric channel 180 which takes advantage of the simplifying properties of the input and output signals of the channel blocks 182 and 184 described above.

Figure 33:
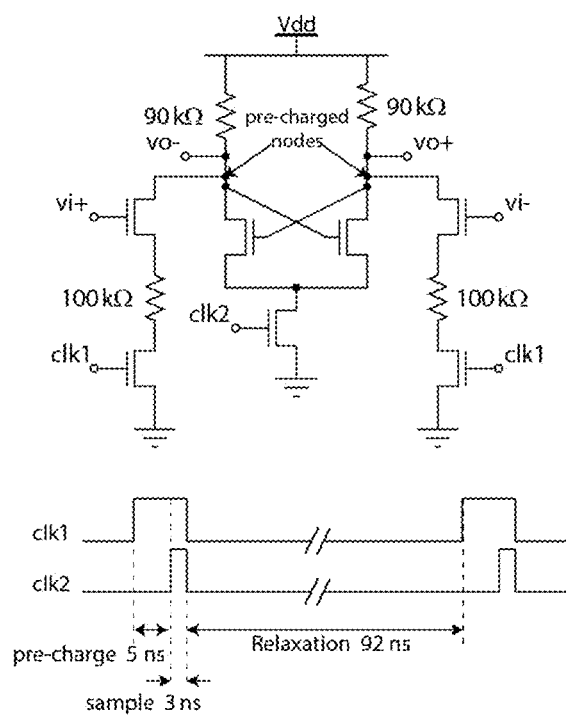
FIG. 33 shows a zero-kickback comparator circuit used to implement the delta-sigma ADC in the proposed channel.
Figure 34:
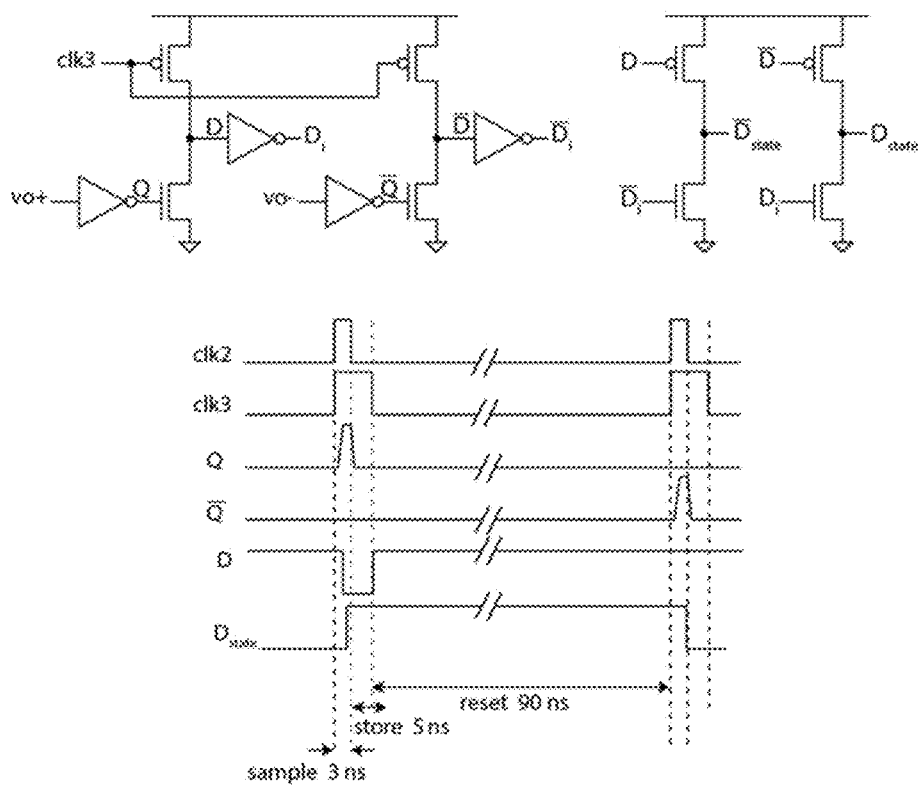
FIG. 34 shows dynamic logic buffers and other pulse shaping circuits necessary for connecting the comparator output to other clock.
Figure 35:
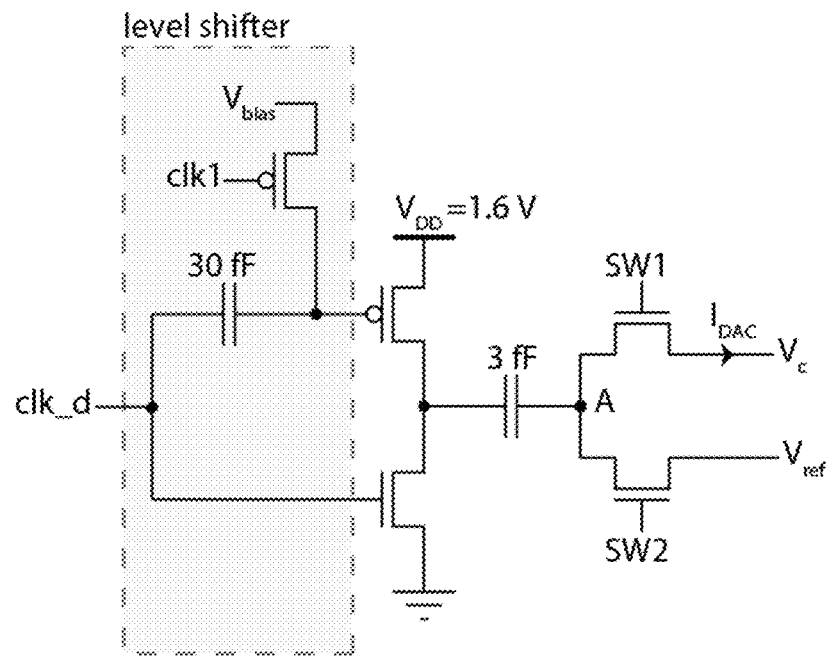
FIG. 35 shows a block diagram of the charge pump to implement the I-DAC in the feedback.

Referring now to FIGS. 33, 34 and 35, shown therein are transistor-level implementations of the different blocks of a delta-sigma ADC circuit provided in view of the embodiments described above. FIG. 33 illustrates a transistor-level schematic of a low power zero-hysteresis zero-kickback latched comparator circuit to implement the delta-sigma ADC in embodiments of the amperometric channel described above. FIG. 34 illustrates dynamic logic buffers and other pulse shaping circuits for connecting the comparator output to other clock, including the I-DAC in the feedback. FIG. 35 illustrates a block diagram of the ultra-low leakage charge pump to implement the I-DAC in the feedback.

Although the foregoing has been described with reference to certain specific embodiments, various modifications thereto will be apparent to those skilled in the art without departing from the spirit and scope of the invention as outlined in the appended claims. The entire disclosures of all references recited above are incorporated herein by reference.

The invention claimed is:

1. An integrated circuit for electrochemically measuring target analytes in a subject comprising:
   a. a recording module array coupled to a plurality of microelectrodes disposable on, in or adjacent to the subject for recording analog signals of analytes of the subject that are chemically bonded to the microelectrodes;
   b. an op-amp-less delta-sigma-analog to digital converter (ADC)-based potentiostat circuit for providing a digitized representation of the recorded analog signals, the potentiostat circuit comprising:
      i. an op-amp-less integrator circuit coupled to the recording module array, the integrator circuit comprising a grounded capacitor for integration of the recorded analog signal;
      ii. a comparator coupled to an output of the integrator circuit to reduce signal distortion thereof;
      iii. a digital-to-analog converter providing a negative feedback loop from an output of the comparator to the output of the integrator circuit; and
      iv. a pulse shaping block providing an output signal of the potentiostat circuit; and
   c. an impedance spectroscopy circuit coupled to the output signal of the potentiostat circuit comprising a 1 bit exclusive-OR (XOR) gate followed by a 1 bit counter for receiving a squarewave and the output signal, and providing a 1 bit approximation of multiplication coefficients using a 1 bit multiplication of the output signal.

2. The integrated circuit of claim 1, wherein the comparator is a zero-hysteresis comparator circuit.

3. The integrated circuit of claim 2, wherein the comparator circuit reduces naturally occurring hysteresis in the comparator by isolating the output of the comparator from its input.

4. The integrated circuit of claim 1, wherein the op-amp-less delta-sigma ADC-based potentiostat circuit is coupled to the recording module array without the need for an intermediary transimpedance amplifier.

5. The integrated circuit of claim 1, wherein the microelectrodes are adapted to be disposed upon the subject's cortex.

6. The integrated circuit of claim 1, wherein the microelectrodes are adapted to be disposed upon the subject's eye.

* * * * *